(12) United States Patent
Sibary et al.

(10) Patent No.: US 12,397,139 B1
(45) Date of Patent: Aug. 26, 2025

(54) GEOMETRIC VOIDS FOR IMPLANTABLE THERAPEUTIC DELIVERY DEVICE

(71) Applicants: Peter Raymond Sibary, Macquarie University (AU); Andrian Sue, Macquarie University (AU); Alexander Stephen Baume, Macquarie University (AU)

(72) Inventors: Peter Raymond Sibary, Macquarie University (AU); Andrian Sue, Macquarie University (AU); Alexander Stephen Baume, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 759 days.

(21) Appl. No.: 16/881,169

(22) Filed: May 22, 2020

Related U.S. Application Data

(60) Provisional application No. 62/851,209, filed on May 22, 2019.

(51) Int. Cl.
*A61N 1/05* (2006.01)
*A61M 31/00* (2006.01)

(52) U.S. Cl.
CPC ............ *A61M 31/00* (2013.01); *A61N 1/0541* (2013.01); *A61M 2210/0668* (2013.01)

(58) Field of Classification Search
CPC .......... A61M 2210/0668; A61M 31/00; A61N 1/0541
See application file for complete search history.

(56) References Cited

U.S. PATENT DOCUMENTS

| | | | |
|---|---|---|---|
| 5,824,049 A * | 10/1998 | Ragheb | A61L 27/54 604/508 |
| 7,571,012 B2 | 8/2009 | Gibson | |
| 8,133,215 B2 | 3/2012 | Gibson | |
| 8,160,714 B2 | 4/2012 | Gibson | |
| 8,190,271 B2 | 5/2012 | Overstreet et al. | |
| 8,271,101 B2 * | 9/2012 | Overstreet | A61K 45/06 607/137 |
| 8,447,409 B2 | 5/2013 | Dadd et al. | |
| 8,504,169 B2 | 8/2013 | Capcelea et al. | |
| 8,515,560 B2 | 8/2013 | Debruyne et al. | |
| 8,538,541 B2 | 9/2013 | Milojevic et al. | |
| 8,617,097 B2 | 12/2013 | Dadd et al. | |
| 8,892,201 B2 | 11/2014 | Parker et al. | |
| 9,008,796 B2 | 4/2015 | Capcelea et al. | |
| 9,026,205 B2 | 5/2015 | Carter et al. | |
| 9,089,450 B2 | 7/2015 | Gibson | |
| 9,101,732 B2 | 8/2015 | Dadd et al. | |
| 9,162,009 B2 | 10/2015 | Rapsey et al. | |
| 9,220,811 B2 * | 12/2015 | Overstreet | A61N 1/0551 |
| 9,616,207 B2 | 4/2017 | Verhoeven et al. | |

(Continued)

*Primary Examiner* — Deanna K Hall
(74) *Attorney, Agent, or Firm* — Piloff Passino & Cosenza LLP; Martin J. Cosenza

(57) ABSTRACT

A device, including an electrode array carrier, that carries one or more electrode arrays, and a therapeutic substance such as for example an anti-inflammatory, wherein the therapeutic substance is located in at least one cavity of the carrier, the cavity having at least one of a non-uniform depth or a non-uniform width with respect to location in a direction of the depth that has an effective impact on a delivery of the therapeutic substance to a human.

48 Claims, 39 Drawing Sheets

(56) References Cited

U.S. PATENT DOCUMENTS

| | | |
|---|---|---|
| 2004/0078057 A1 | 4/2004 | Gibson |
| 2006/0287689 A1* | 12/2006 | Debruyne ............ A61K 9/0046 607/57 |
| 2007/0213799 A1* | 9/2007 | Jolly ................... A61N 1/0541 607/137 |
| 2008/0033520 A1 | 2/2008 | Jolly |
| 2011/0288500 A1 | 11/2011 | Dadd et al. |
| 2012/0046702 A1 | 2/2012 | Gibson |
| 2014/0155811 A1 | 6/2014 | Gibson |
| 2014/0315789 A1 | 10/2014 | Willcox et al. |
| 2017/0340485 A1 | 11/2017 | Verhoeven et al. |

* cited by examiner

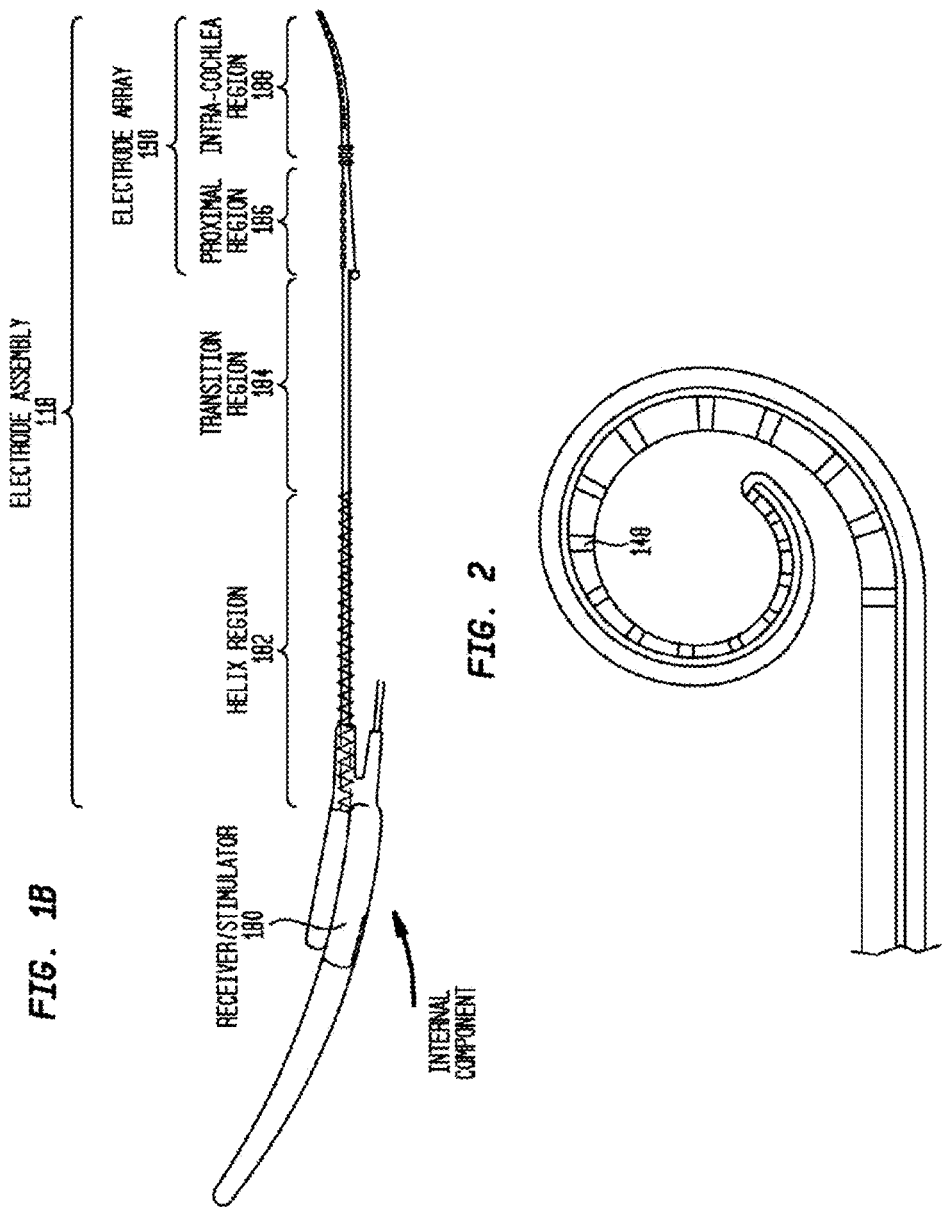

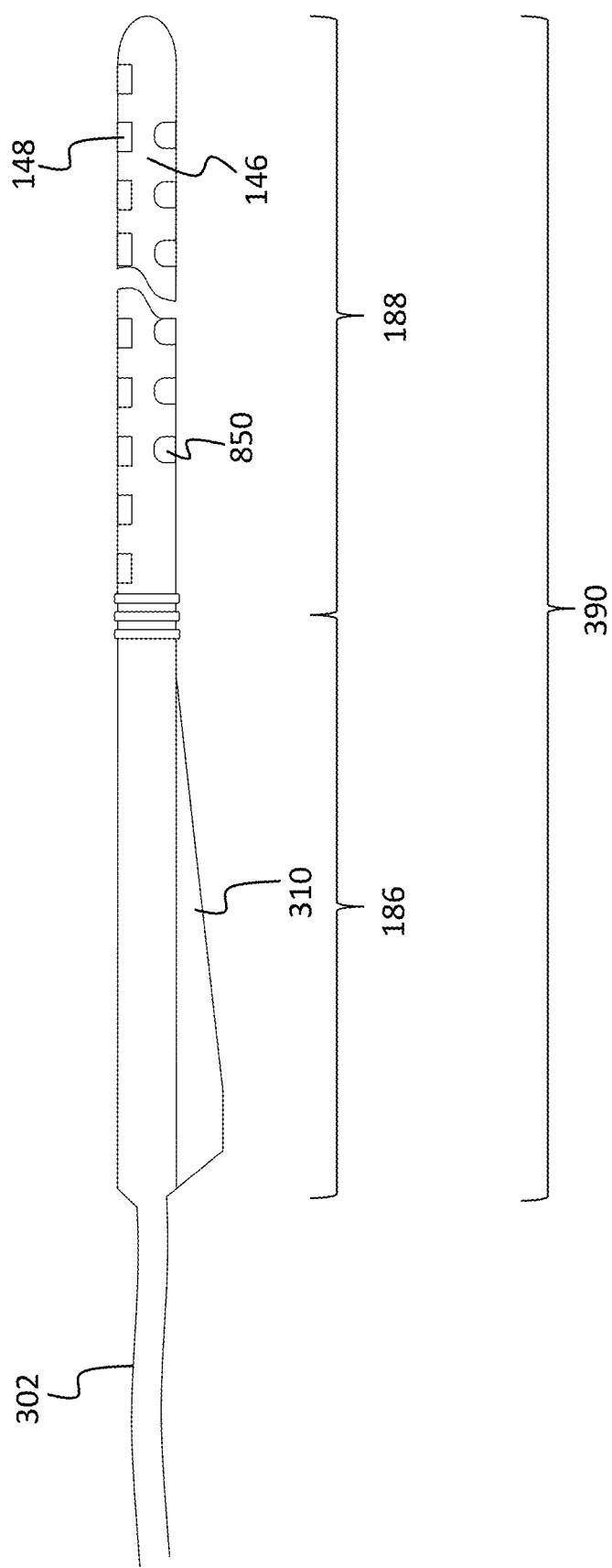

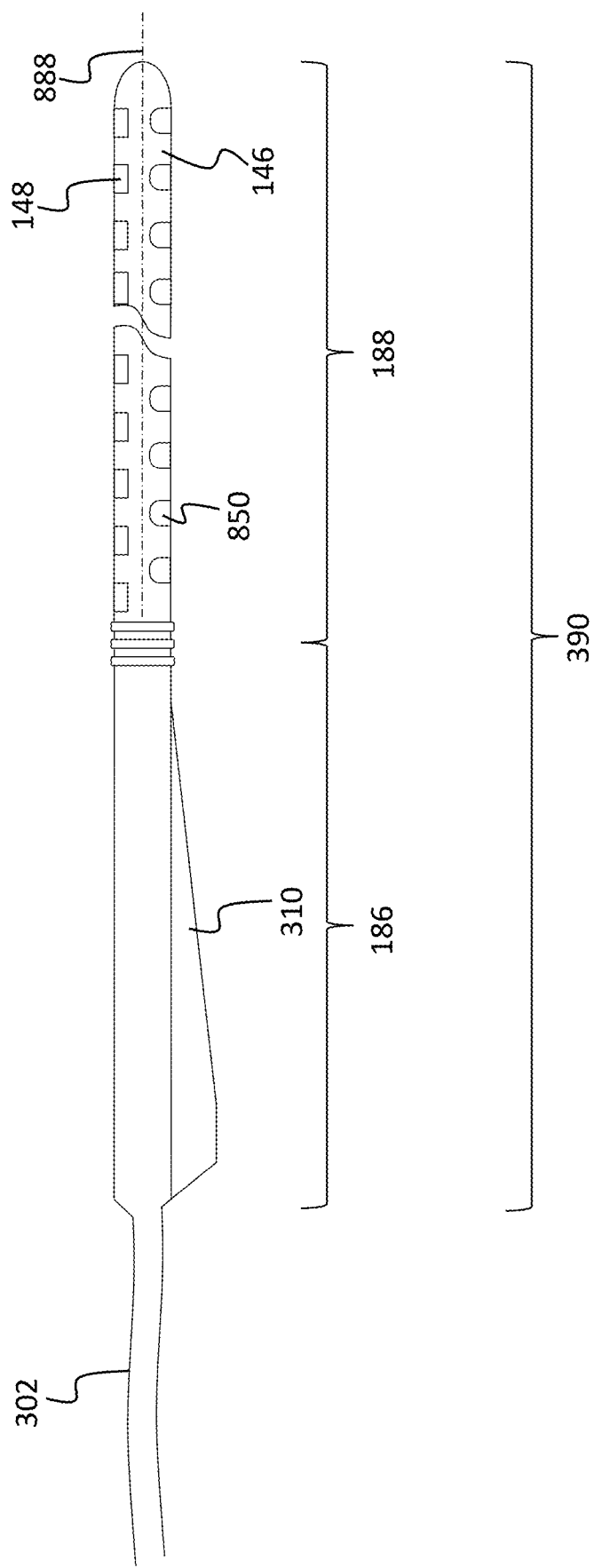

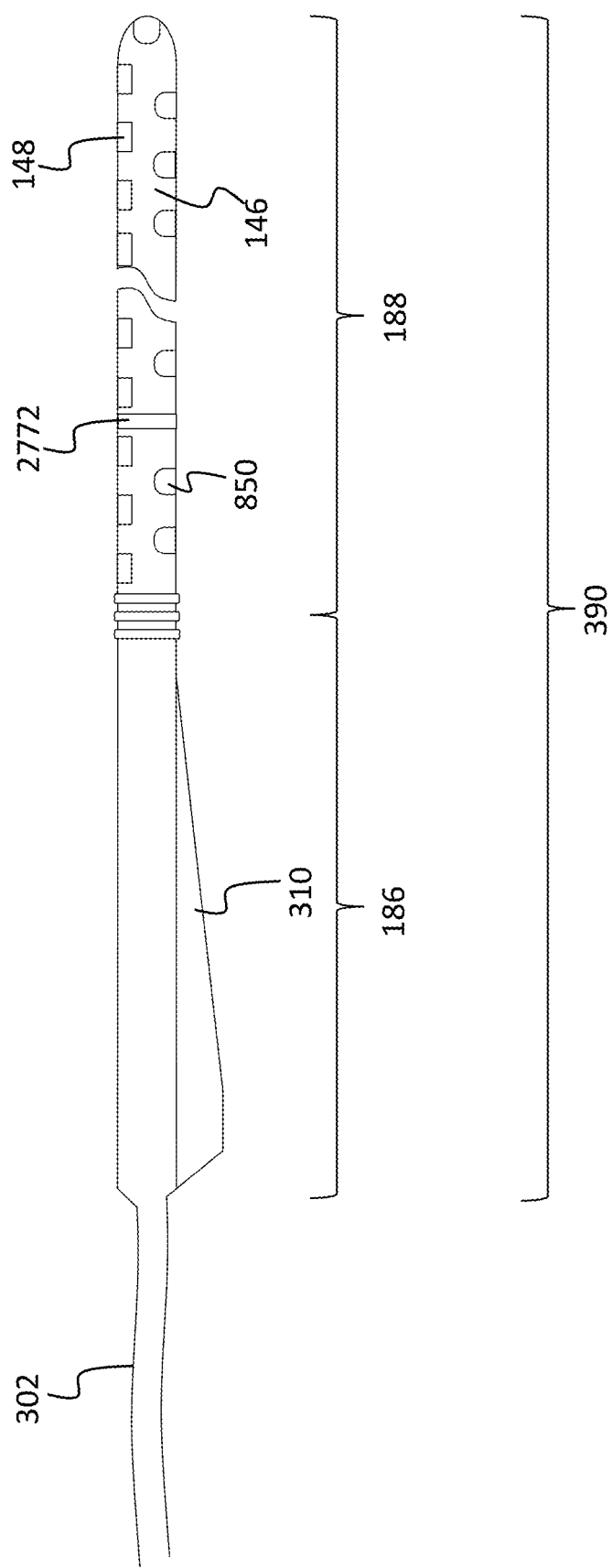

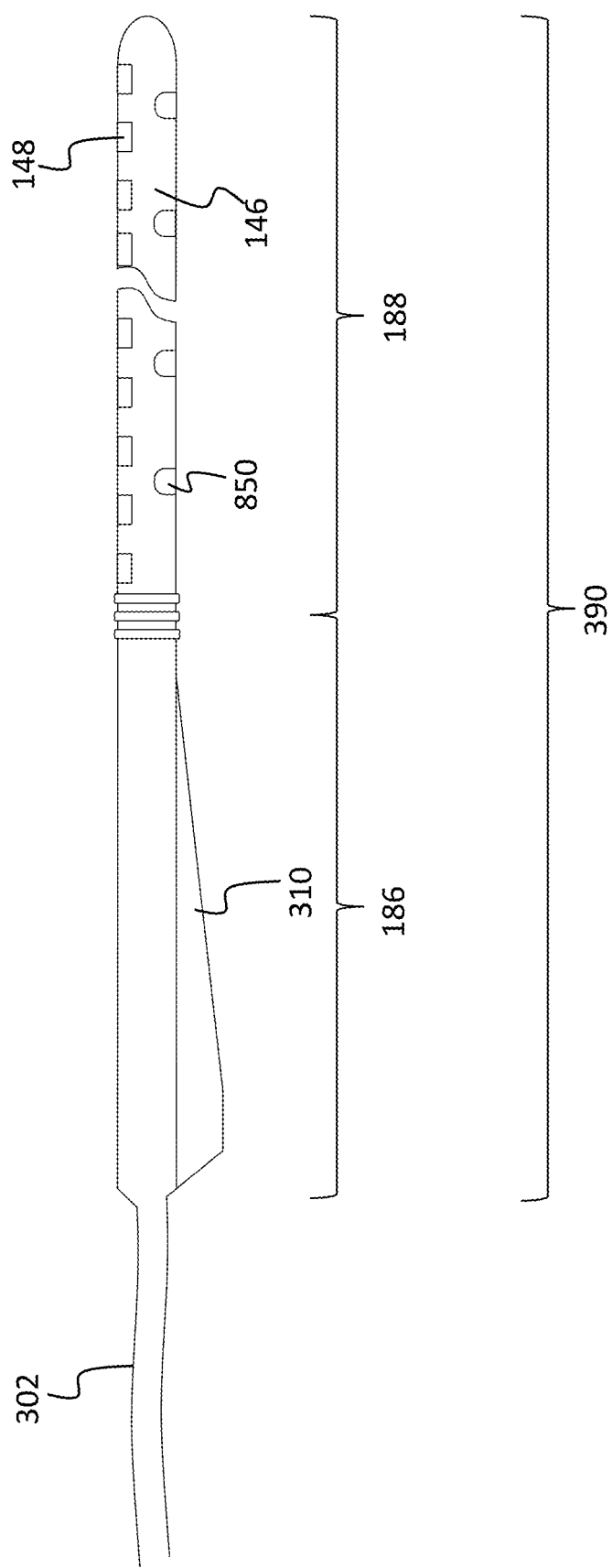

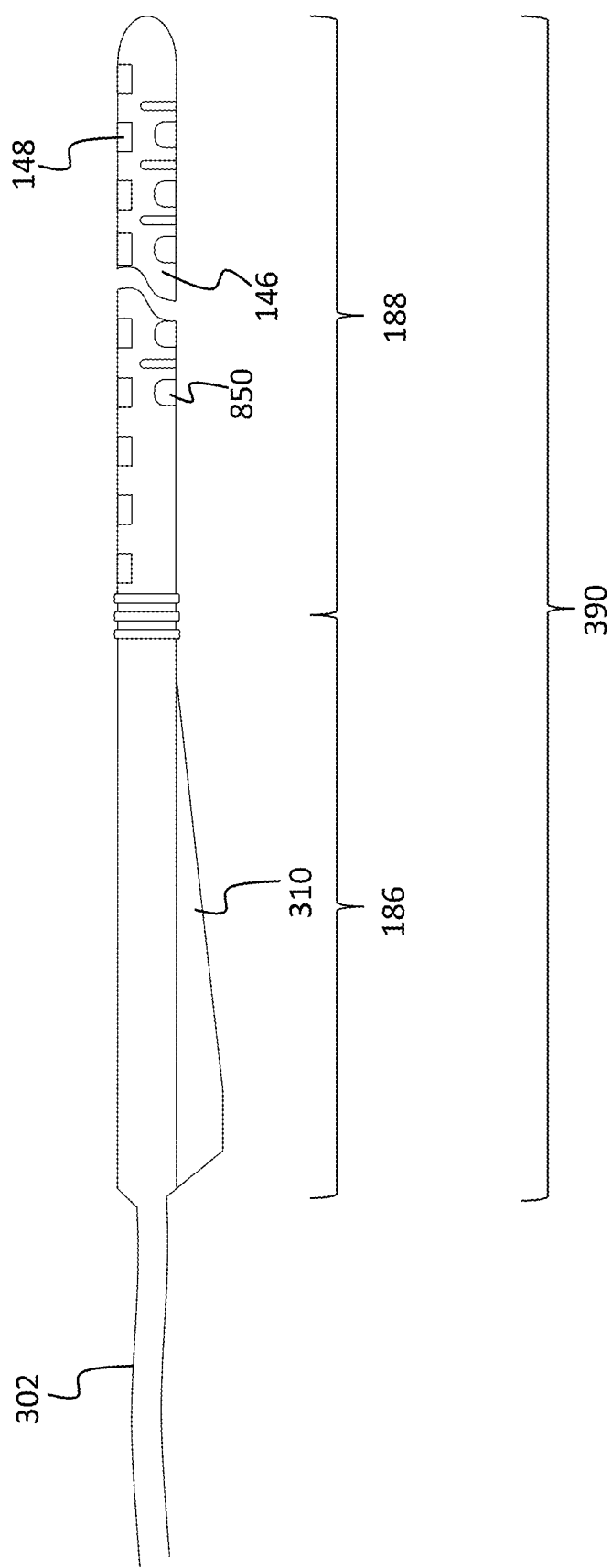

GEOMETRIC VOIDS FOR IMPLANTABLE THERAPEUTIC DELIVERY DEVICE

CROSS-REFERENCE TO RELATED APPLICATIONS

This application claims priority to Provisional U.S. Patent Application No. 62/851,209, entitled GEOMETRIC VOIDS FOR IMPLANTABLE THERAPEUTIC DELIVERY DEVICE, filed on May 22, 2019, naming Peter Raymond SIBARY of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In an exemplary embodiment, there is a device, comprising an electrode array carrier and a therapeutic substance, wherein the therapeutic substance is located in a well of the electrode array carrier.

In an exemplary embodiment, there is a device, comprising an electrode array carrier and a therapeutic substance, wherein the therapeutic substance is located in at least one cavity of the carrier, the cavity having at least one of a non-uniform depth or a non-uniform width with respect to location in a direction of the depth that has an effective impact on a delivery of the therapeutic substance to a human.

In an exemplary embodiment, there is a method, comprising delivering a therapeutic substance to a cochlea of a recipient by elution from a cochlear implant electrode array carrier, wherein an elution rate by weight over a period of time is variable owing to a geometry of the carrier containing the therapeutic substance.

In an exemplary embodiment, there is an a device, comprising an electrode array carrier; and a therapeutic substance, wherein at least one of the electrode array carrier and the therapeutic substance are collectively arranged to provide for a therapeutic substance release rate that is variable over time or the therapeutic substance is located in a plurality of wells that are spaced apart from one another, at least some of the wells being located in pairs at a same distance along a longitudinal axis of the carrier.

In an exemplary embodiment, there is a method, comprising obtaining an electrode array carrier having therein a plurality of voids, the electrode array carrier being a stock electrode carrier and the voids being common to other electrode array carriers of the stock and providing a therapeutic substance into at least one of the voids, wherein the action of providing the therapeutic substance into the at least one of the voids results in a specific therapeutic substance delivery profile when the electrode array carrier is implanted in a human.

BRIEF DESCRIPTION OF THE DRAWINGS

Embodiments of the present invention are described below with reference to the attached drawings, in which:

FIG. 1B is a side view of the implantable components of the cochlear implant;

FIG. 2 is a side view of an embodiment of the electrode array illustrated in FIGS. 1A and 1B in a curled orientation;

FIGS. 15-19 and 27 present side views of exemplary embodiments of exemplary electrode array assemblies;

DETAILED DESCRIPTION

Figure 1A:
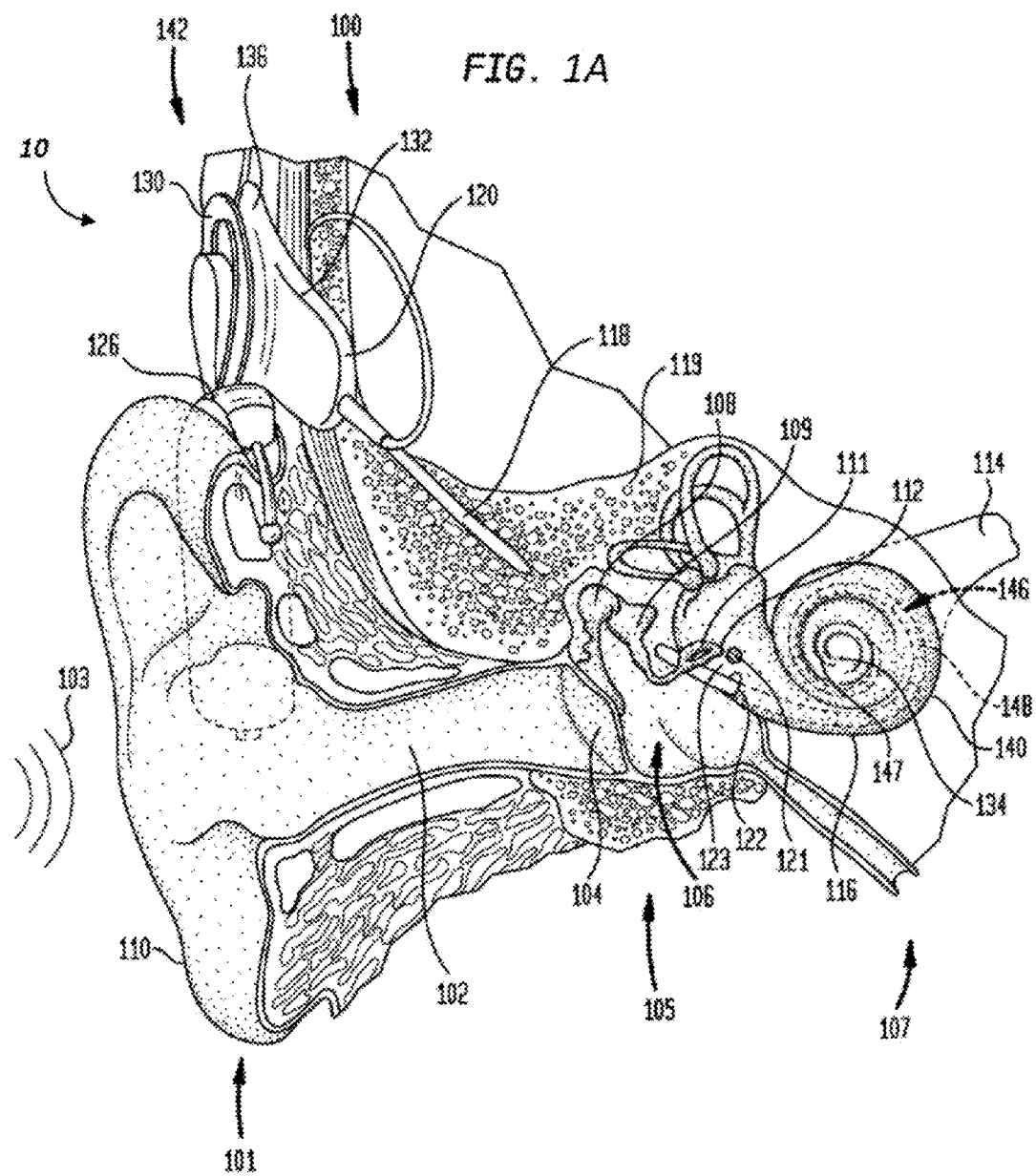
FIG. 1A is a perspective view of an exemplary hearing prosthesis utilized in some exemplary embodiments.

FIG. 1A is perspective view of a totally implantable cochlear implant, referred to as cochlear implant 100, implanted in a recipient. The totally implantable cochlear implant 100 is part of a system 10 that can include external components, as will be detailed below.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate stimulating assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate stimulating assembly 118.

Elongate stimulating assembly 118 has a proximal end connected to main implantable component 120, and a distal end implanted in cochlea 140. Stimulating assembly 118 extends from main implantable component 120 to cochlea 140 through mastoid bone 119. In some embodiments stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of electrodes 148, disposed along a length thereof. As noted, a stimulator unit generates stimulation signals which are applied by stimulating contacts 148, which, in an exemplary embodiment, are electrodes, to cochlea 140, thereby stimulating auditory nerve 114. In an exemplary embodiment, stimulation contacts can be any type of component that stimulates the cochlea (e.g., mechanical components, such as piezoelectric devices that move or vibrate, thus stimulating the cochlea (e.g., by inducing movement of the fluid in the cochlea), electrodes that apply current to the cochlea, etc.). Embodiments detailed herein will generally be described in terms of an electrode assembly 118 utilizing electrodes as elements 148. It is noted that alternate embodiments can utilize other types of stimulating devices. Any device, system, or method of stimulating the cochlea via a device that is located in the cochlea can be utilized in at least some embodiments. In this regard, any implantable array that stimulates tissue, such as a retinal implant array, or a spinal array, or a pace maker array, etc., is encompassed within the teachings herein unless otherwise noted.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100 is a traditional hearing prosthesis.

While various aspects of the present invention are described with reference to a cochlear implant (whether it be a device utilizing electrodes or stimulating contacts that impart vibration and/or mechanical fluid movement within the cochlea), it will be understood that various aspects of the embodiments detailed herein are equally applicable to other stimulating medical devices having an array of electrical simulating electrodes such as auditory brain implant (ABI), functional electrical stimulation (FES), spinal cord stimulation (SCS), penetrating ABI electrodes (PABI), and so on. Further, it should be appreciated that the present invention is applicable to stimulating medical devices having electrical stimulating electrodes of all types such as straight electrodes, perimodiolar electrodes and short/basilar electrodes. Also, various aspects of the embodiments detailed herein and/or variations thereof are applicable to devices that are non-stimulating and/or have functionality different from stimulating tissue, such as for, example, any intra-body dynamic phenomenon (e.g., pressure, or other phenomena consistent with the teachings detailed herein) measurement/sensing, etc., which can include use of these teachings to sense or otherwise detect a phenomenon at a location other than the cochlea (e.g., within a cavity containing the brain, the heart, etc.). Additional embodiments are applicable to bone conduction devices, Direct Acoustic Cochlear Stimulators/Middle Ear Prostheses, and conventional acoustic hearing aids. Any device, system, or method of evoking a hearing percept can be used in conjunction with the teachings detailed herein.

FIG. 1B is a side view of the internal component of cochlear implant 100 without the other components of system 10 (e.g., the external components). Cochlear implant 100 comprises a receiver/stimulator 180 (combination of main implantable component 120 and internal energy transfer assembly 132) and a stimulating assembly or lead 118. Stimulating assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity subsection of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

FIG. 2 is a side view of electrode array assembly 190 in a curled orientation, as it would be when inserted in a recipient's cochlea, with electrode contacts 148 located on the inside of the curve. FIG. 2 depicts the electrode array of FIG. 1B in situ in a patient's cochlea 140.

Figure 3:
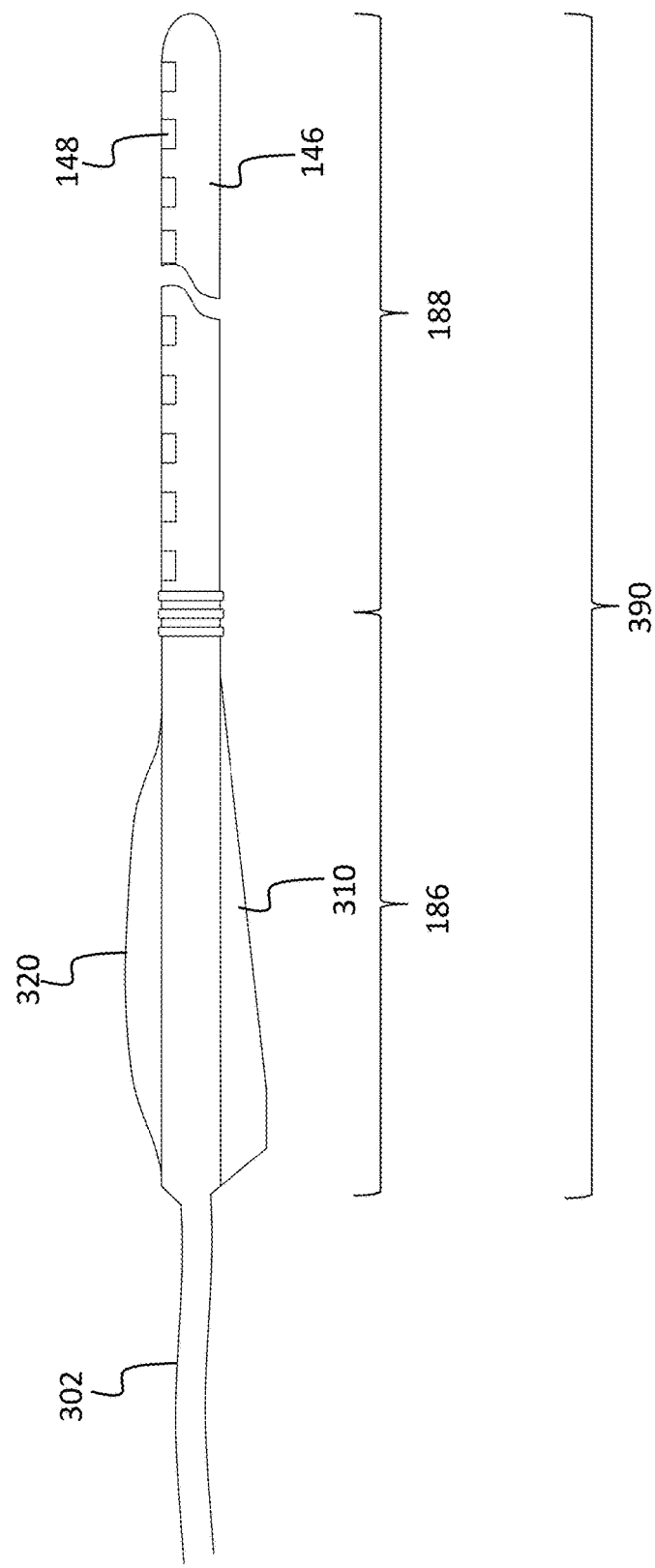
FIG. 3 is a side view of an exemplary electrode array assembly.

FIG. 3 depicts a side view of a device 390 corresponding to a cochlear implant electrode array assembly that can include some or all of the features of electrode array assembly 190 of FIG. 1B. More specifically, in an exemplary embodiment, stimulating assembly 118 includes electrode array assembly 390 instead of electrode array assembly 190 (i.e., 190 is replaced with 390).

Electrode array assembly 390 includes a cochlear implant electrode array componentry of the 190 assembly above. Note also element 310, which is a quasi-handle like device utilized with utilitarian value vis-à-vis inserting the 188 section into a cochlea. By way of example only and not by way of limitation, element 310, which is a silicone body that extends laterally away from the longitudinal axis of the electrode array assembly 390, and has a thickness that is less than that of the main body of the assembly (the portion through which the electrical leads that extend to the electrodes extend to the elongate lead assembly 302). The thickness combined with the material structure is sufficient so that the handle can be gripped at least by a tweezers or the like during implantation and by application of a force on to the tweezers, the force can be transferred into the electrode array assembly 390 so that section 188 can be inserted into the cochlea.

Also presented in FIG. 3 is reservoir 320. In some instances, reservoir 320 is configured to contain a bioactive substance or otherwise some form of mass that has fluid properties. In some instances, the reservoir 320 is in fluid communication with one or more portions of the electrode array making up section 188, as will be described in greater detail below. First however, some exemplary features of the reservoir will now be described.

Figure 4:
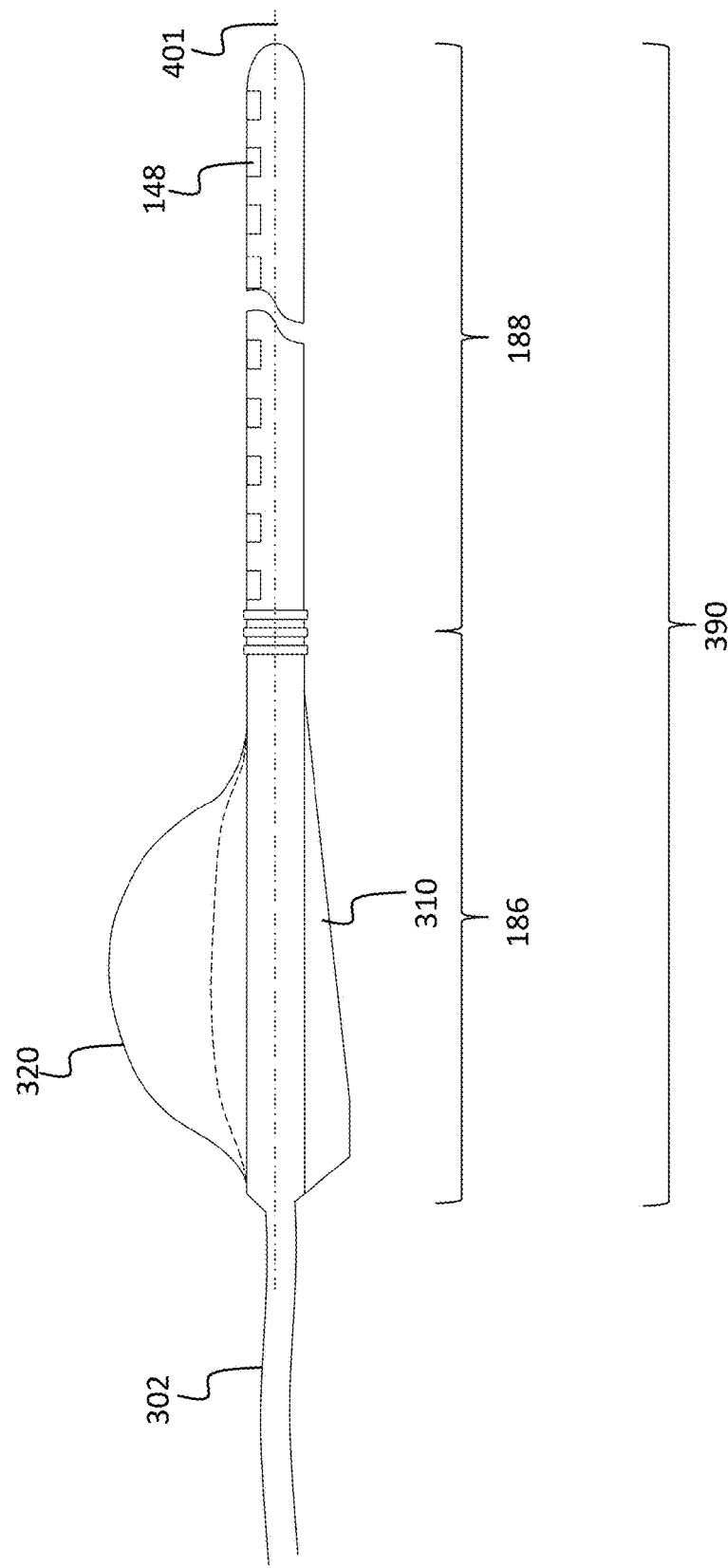
FIG. 4 is a side view of the array of FIG. 3 in a different state.

In some instances, the reservoir is an expandable reservoir. By way of example only and not by way of limitation, in some instances, the reservoir is made out of an elastomeric material and forms an elastomeric enclosure. In some instances, in a relaxed state, the reservoir 320 establishes a first interior volume and takes up a first exterior volume. When in an expanded state, the reservoir 320 establishes a second interior volume that is larger than the first interior volume, and also takes up a second exterior volume that is larger than the first exterior volume. FIG. 4 depicts an exemplary scenario of expansion of reservoir 320. In an exemplary some instances, the second interior volume is less than, greater than or equal to 1.25, 1.5, 1.75, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 or more times the first interior volume. In some instances, the second exterior volume is less than, greater than, or equal to 1.25, 1.5, 1.75, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 100, 125, 150, 175, or 200 or more times the first exterior volume or any value or range of values therebetween on 0.01 increments). With respect to the exterior volume, this is the volume that is taken up by the reservoir itself and not the other components. That said, in some instances, one can consider the entire electrode array assembly to establish a first overall exterior volume when the reservoir 320 is in the relaxed state, and a second overall exterior volume when the reservoir 320 is expanded. In some instances, the second overall exterior volume is less than, greater than or equal to 1.25, 1.5, 1.75, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 or more times the first overall exterior volume.

In some instances, the electrode array assembly 390 and/or the apparatus of which is a part, such as the implantable component of the cochlear implant, is configured to enable the reservoir to be filled after the electrode array assembly 390 is implanted in the recipient.

In some instances, the aforementioned expansions can also occur after the electrode array has been inserted, including fully inserted, into the cochlea. In some instances, the filling of the reservoir can occur during the surgical operation and/or can occur after the surgical operation (as will be described in greater detail below). By during the surgical operation, it is meant while the opening accessing the middle ear cavity and the outside of the cochlea is open. This as distinguished from the temporal period after the opening is closed, which temporal period can encompass a period of time while the recipient is still in the operating room. Again, some of the features that enable the reservoir to be filled after the surgery will be described in greater detail below (and some of the features that enable the reservoir to be filled during the surgery will also be described).

It is briefly noted that frequently, the phrase "drug" will be utilized herein. Embodiments are directed towards a drug delivery system. However, embodiments are not so limited unless otherwise specified. In this regard, embodiments are directed towards a therapeutic substance delivery system. Therapeutic substances include drugs, but also include non-drug substances. In an exemplary embodiment, therapeutic substances include steroids and biologics. Therapeutic substances can also include minerals and the like. Any disclosure herein of drug or the containment of drug or the delivery of drug also corresponds to another embodiment that corresponds to an embodiment that is directed towards a therapeutic substance. That is, typically, the word drug used herein is shorthand for therapeutic substance. Accordingly, embodiments include the present disclosure where the word drug is replaced by the word therapeutic substance, unless otherwise specified.

Figure 5:
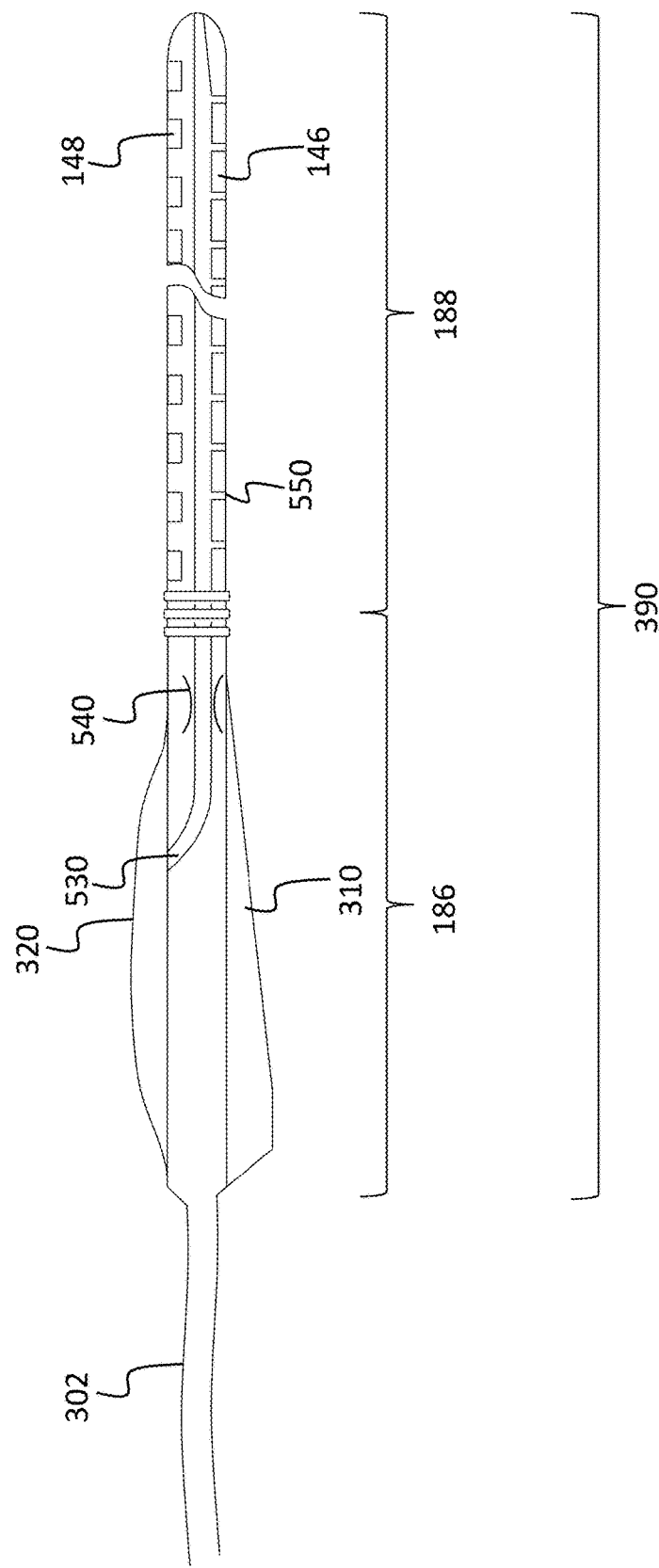
FIGS. 5 and 6 and 7 are side views of exemplary electrode array assemblies.

FIG. 5 depicts a cross-sectional view of the electrode array assembly 390 with the reservoir 320 in the relaxed state. As can be seen, conduit 530 extends from the reservoir into section 188, and then along the length of section 188. Also as can be seen, sub conduits extend radially away from the longitudinal axis of the conduit 530, and lead to orifices 550, the system enabling mass flow from the reservoir 320 into the cochlea. As can be seen in this example, an optional flow restrictor 540 is located in section 186, between the reservoir 320 and the intracochlear portion/the orifices that lead into the cochlea. Alternatively, and/or in addition to this, flow restrictor 540 can be located in section 188. The utility of the flow restrictor will be described in greater detail below. In some instances, the flow restrictor is a membrane or the like, such as a restrictive membrane, that enables the controlled release of the therapeutic substance. In some instances, instead of the reservoir 320 and/or in addition to the reservoir 320, conduit 530 can be connected via a fluidic device, such as a tube, to a component away from the array such that fluid can be transported to the conduit 530 for delivery to the cochlea.

Figure 6:
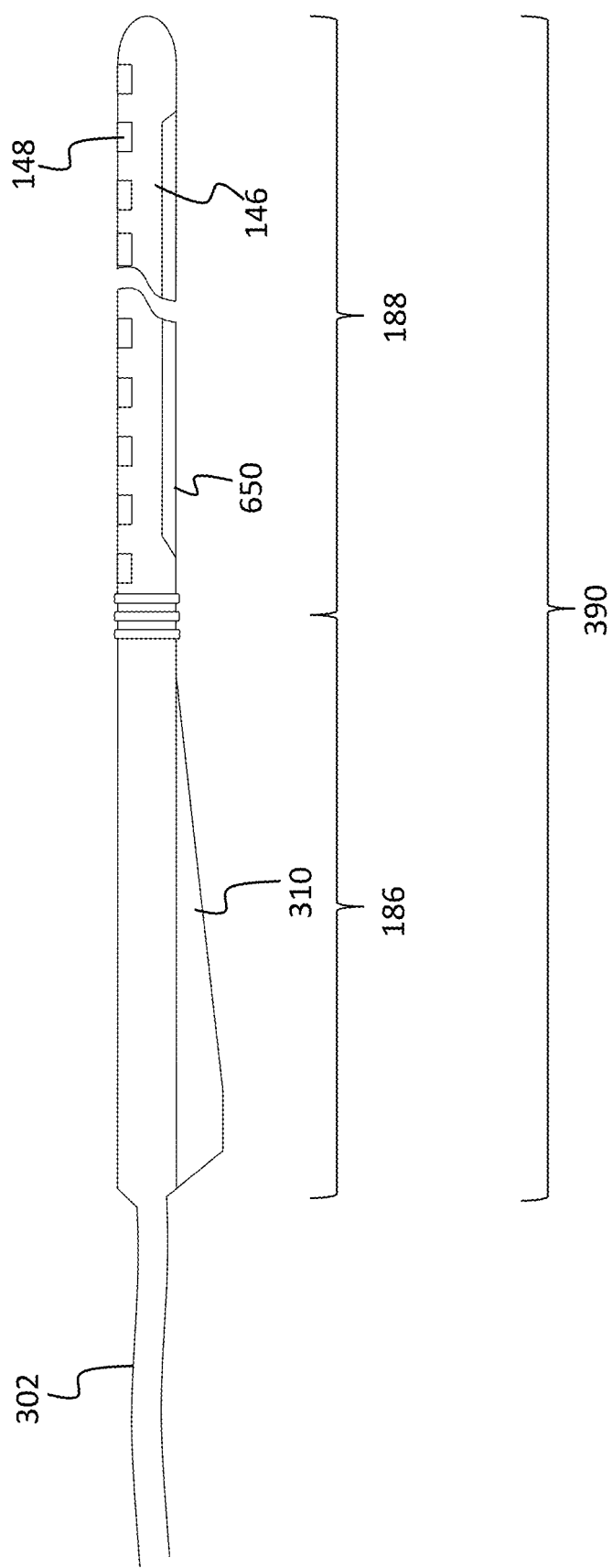

FIG. 6 presents an exemplary cochlear implant electrode array that includes a backstrap 650. In some instances, the backstrap is a solid component that is made up of or otherwise includes a drug or other therapeutic substance. In some instances, the backstrap can be drug impregnated silicone component that is located within the silicone body that constitutes the carrier of the electrodes 148. This can, in some instances, be the same silicone or can be different than the silicone that makes up the carrier. In some instances, the backstrap 650 can be made of a plastic component or other component that can be flexible in a manner that permits the cochlear implant electrode array to curl inside the cochlea. In some instances, the backstrap dissolves in part or in whole to transfer the drug into the cochlea/the perilymph of the cochlea. In an exemplary embodiment, the therapeutic substance or drug can elute from the backstrap.

In some instances, the backstrap can be a tube that contains a fluid that is or contains a drug or other therapeutic substance. In an exemplary embodiment, the drug can elute through the tube, diffuse through the tube, etc., to reach the tissue of the cochlea/perilymph of the cochlea.

Figure 7:
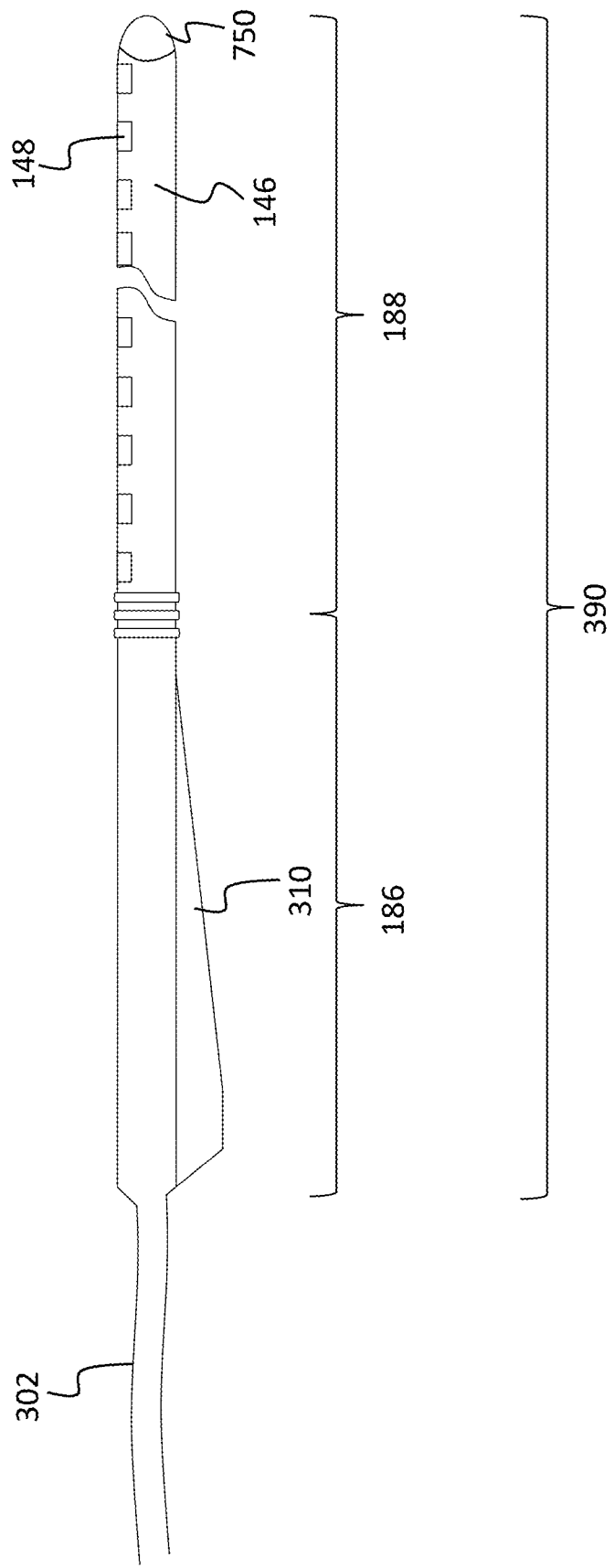

FIG. 7 presents an exemplary cochlear implant that utilizes a so-called "soft tip" 750 at the tip of the electrode array. In this regard, the soft tip 750 can be a silicone body that is impregnated with a therapeutic substance or can be a reservoir that contains a therapeutic substance, etc. In some instances, the tip is a discreet component from the rest of the array in that it comprises different materials aside from the fact that it contains a drug or otherwise contains a therapeutic substance.

By way of example only and not by way of limitation, in some instances, the anti-inflammatory drug Dexamethasone can be mixed into an uncured silicone and then applied to the electrode carrier and then cured. In some instances, this can establish the backstrap detailed above, which in a sense can be considered a spine along the lateral surface of the carrier. This regime can also be utilized to establish the soft tip, albeit that the application of the uncured silicone would be located at the tip. This can be used in the embodiments below.

In at least some exemplary embodiments, the embodiments detailed below can provide a therapeutic dosage of therapeutic substance into the cochlea for at least or no more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 80, 90, 100, 110, 120 days or more, or any value or range of values therebetween in one day increments (e.g., 37-92 days, 88 days, 111 days, etc.).

In at least some instances of the devices detailed above, there is an impact on the mechanical properties of the electrode array in that the structure of the electrode array that would otherwise be present is replaced by the drug delivery components. In at least some instances, this impact on the mechanical product for these can be deleterious with respect to that which would otherwise be the case in the absence of the utilization of such. Some embodiments of the teachings detailed herein reduce and/or avoid the impact.

Figure 8:
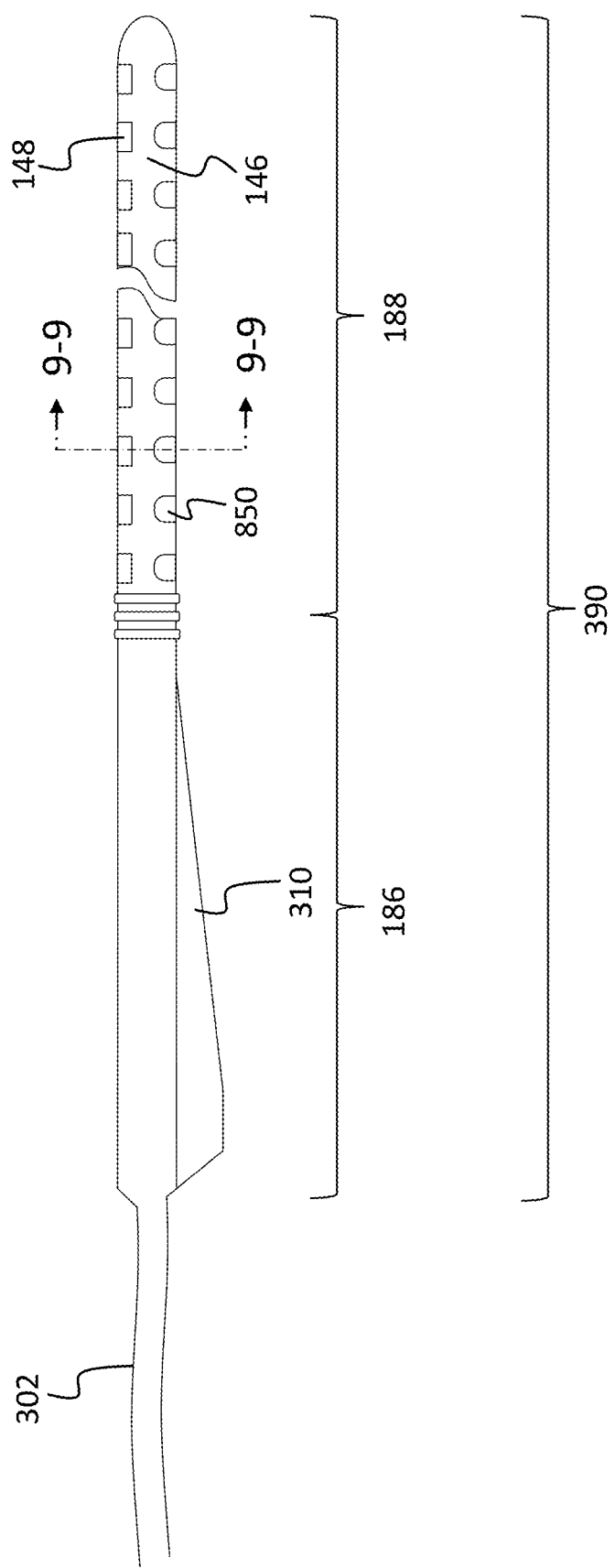
FIG. 8 presents a side view of an exemplary embodiment of an exemplary electrode array assembly.

FIG. 8 presents an exemplary embodiment of an electrode array assembly that utilizes wells 850 that are spaced along at least a portion of the length of the intracochlear portion 188. In some exemplary embodiments, but not necessarily in all exemplary embodiments, this arrangement can alleviate at least some if not all of the above-noted impact to the mechanical properties of the electrode array. In an exemplary embodiment, this arrangement can reduce the deleterious impact, to the extent such exists, when the mechanical properties the electrode array relative to that which would otherwise be the case relative to one or more of the above embodiments. Thus, in an exemplary embodiment, the well(s) are located in a low stress area (which includes a no-stress area) of the electrode array carrier such that the well does not effective affect a bulk mechanical characteristic of the electrode array relative to that which would be the case in the absence of the well, all other things being equal. Also, in an exemplary embodiment, the wells are located such that any stress that exists in the array has no effective impact on the well, all other things being equal.

Figure 9:
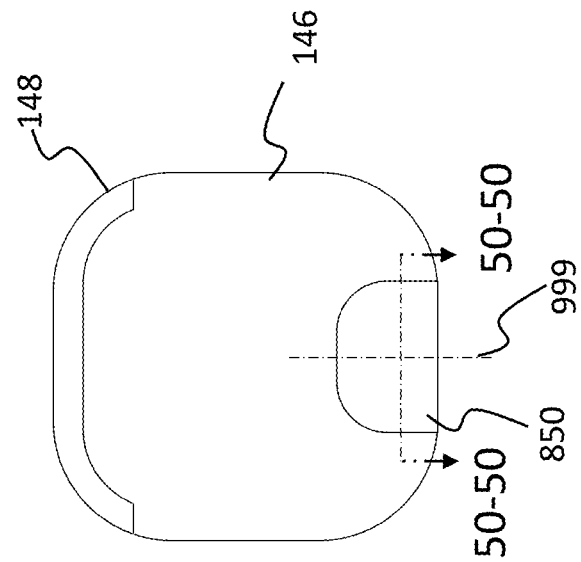
FIGS. 9-14 and 20-26 and 31 present views looking down the longitudinal axis of some arrays according to some exemplary embodiments.
Figure 10:
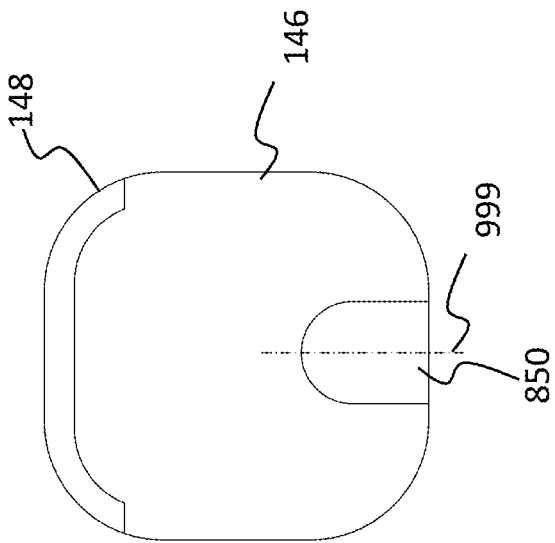
Figure 12:
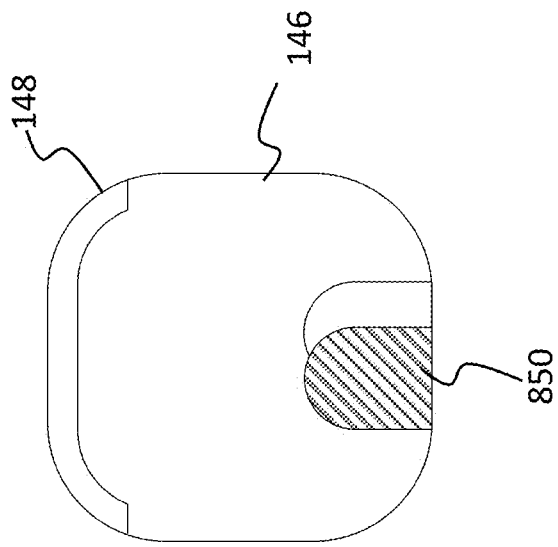
Figure 11:
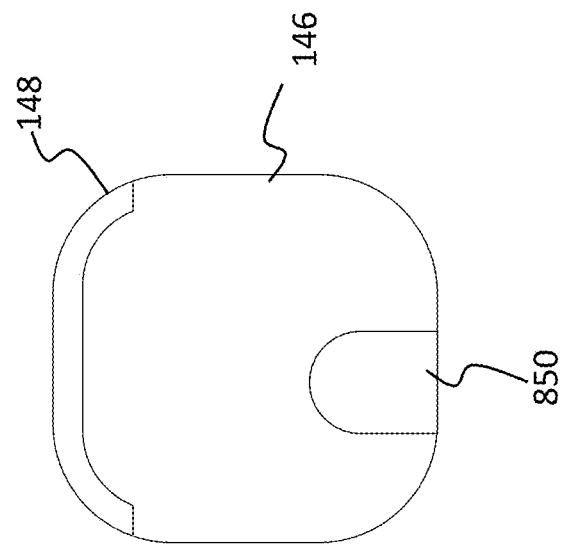

FIG. 8 depicts wells 850 that are aligned with respect to the longitudinal axis with the electrodes 148. In this regard, a cross-section through the electrode array, such as seen in FIG. 9, would have the wells 850 and the electrodes 148 basically divided evenly on one side of the cut versus the other side of the cut (cross-hatching is not shown—note that this is for description—the hatching actually represents a void (albeit one that is filled with drug/silicone and drug, etc.)). It is briefly noted that the configurations of the wells can be different, such as that seen in FIG. 10, which shows a wider and shorter well 850. Additional details of this will be described below. It is noted that the wells need not be located symmetrically along the center plane to the longitudinal axis of the array. This can be seen in FIG. 11, where the well 850 is located to the left of the plane, or more accurately, the geometric center of the well is located to the left of that plane. It is also noted that the wells need not necessarily be aligned the same way. In this regard, FIG. 12 depicts a cross-section through a well 850, where the next well can be seen in the background where the center of gravity thereof is located to the right of the plane that would extend to the longitudinal axis/geometric center of the electrode array 146 in the vertical direction. In view of the above, it can be seen that some embodiments include a plurality of wells spaced apart from one another, and a majority of the wells are aligned along a longitudinal axis of the carrier with electrodes thereof. In an embodiment, 50.1, 55, 60, 65, 70, 75, 80, 85, 90, 91, 92, 93, 94, 95, 96, 97, 98, 99, or 100 percent of the wells (or any value or range of values therebetween in 0.1% increments) are so aligned. By aligned, it is meant that the geometric centers of the electrodes and the wells lie on the same plane with respect to the plane that is normal to the longitudinal axis of the array. In an exemplary embodiment, a majority of the wells are located along the longitudinal axis of the carrier such that at least a portion of the well and/or the entirety of the well is "shadowed" by a an electrode (i.e., looking downward from the basal side of the electrode array (the side with the electrodes) with the electrode array perfectly straight (whether in a natural state or artificially held) a plane that passes through any part of the electrode, which plane is normal to the longitudinal axis, also extends through at least a portion of the well. In an exemplary embodiment, any of the aforementioned percentages detailed with respect to the alignment are applicable to this arrangement as well.

Figure 13:
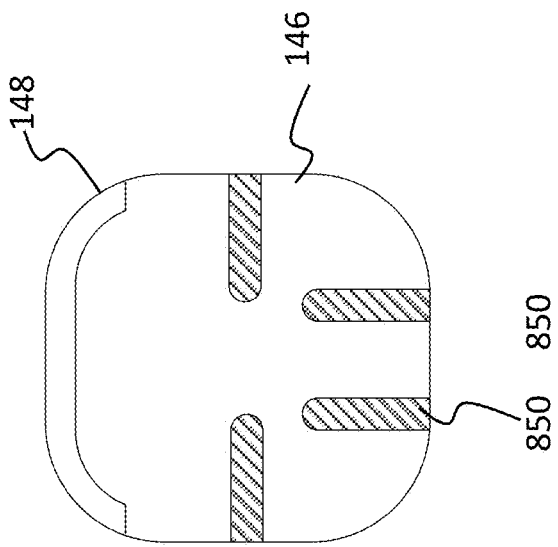
Figure 14:
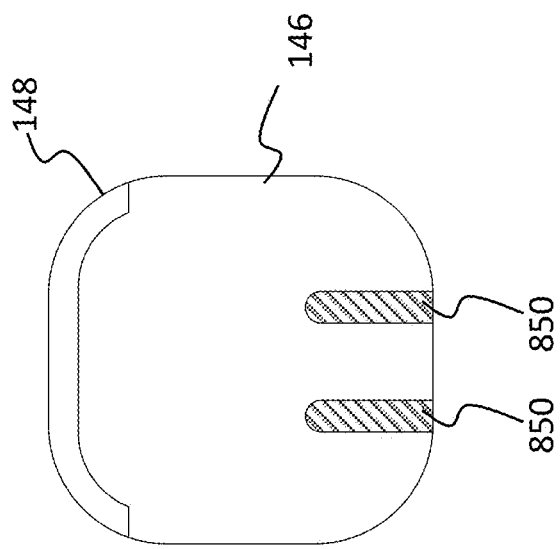

FIG. 13 depicts another exemplary embodiment where there is a plurality of wells at a given cross-section along the longitudinal axis of the electrode array. In this exemplary embodiment, there are two wells 850 that can be seen in the cross-section at the location taken with reference to FIG. 9. That said, in an alternate embodiment, additional wells or fewer wells can be located at such cross-section. Any number of wells in any configuration that can enable the teachings detailed herein can be utilized in at least some exemplary embodiments. Indeed, FIG. 14 depicts another exemplary embodiment where the wells 850 extend from services other than the lateral surface of the electrode array. In this regard, there are two wells that extend from the lateral surface of the electrode array (the bottom), and one well each that extends from the flanks of the electrode array with respect to this cross-section—it is to be understood that this arrangement can be repeated along the length of the electrode array—it is also to be understood that alternate arrangements can be located at different cross-sections—any arrangement at one cross-section disclosed herein that can be utilized to enable the teachings detailed herein can be utilized at one cross-section, and another cross-section can have another arrangement as disclosed herein or variations thereof, provided that such arrangement can enable the teachings detailed herein.

In view of the above, it can be seen that some embodiments include a plurality of wells spaced apart from one another, and a majority of the wells are not aligned along a longitudinal axis of the carrier with electrodes thereof. In an embodiment 50.1, 55, 60, 65, 70, 75, 80, 85, 90, 91, 92, 93, 94, 95, 96, 97, 98, 99, or 100 percent of the wells (or any value or range of values therebetween in 0.1% increments) are not aligned. In an exemplary embodiment, a majority of the wells are located along the longitudinal axis of the carrier such that at least a portion of the well is not "shadowed" by an electrode (i.e., looking downward from the basal side of the electrode array (the side with the electrodes) with the electrode array perfectly straight (whether in a natural state or artificially held) a plane that passes through any part of the electrode, which plane is normal to the longitudinal axis, also extends through at least a portion of the well. In an exemplary embodiment, any of the aforementioned percentages are also applicable. In an embodiment 50.1, 55, 60, 65, 70, 75, 80, 85, 90, 91, 92, 93, 94, 95, 96, 97, 98, 99, or 100 percent of the wells (or any value or range of values therebetween in 0.1% increments) are not aligned. In an exemplary embodiment, a majority of the wells are located along the longitudinal axis of the carrier such that no portion of the well is "shadowed" by an electrode (i.e., looking downward from the basal side of the electrode array (the side with the electrodes) with the electrode array perfectly straight (whether in a natural state or artificially held) a plane that passes through any part of the electrode, which plane is normal to the longitudinal axis, also extends through at least a portion of the well). In an exemplary embodiment, any of the aforementioned percentages are also applicable.

The embodiment of FIG. 8 depicts wells that are aligned along the longitudinal axis of the electrode array with respective electrodes 148. In the exemplary embodiment shown, there is a one to one or a two to one or a three to one or a four to one, etc., relationship, with respect to the respective electrodes. In the embodiments of FIGS. 8 and 9, for every electrode, there is a well. In alternative embodiments, there may not necessarily be wells that are aligned with each electrode. This can be seen in FIG. 15, where, for example, the first two electrodes and the last electrodes have no respective well. (Note that this is simply a spatial relationship that is being described. In at least some exemplary embodiments, the wells are completely separate and have nothing to do with the electrodes.) While the embodiments of FIGS. 8 and 15 depict the geometric centers of the wells being aligned with the geometric centers of the electrodes (they basically lie on the same plane that is normal with respect to the longitudinal axis of the array), other embodiments are such that the geometric centers of the wells are not aligned with the geometric centers of the electrodes. This is seen in FIG. 16, where, for example, at least some of the wells located such that the center geometric centers thereof are offset from the geometric centers of the electrode array along the longitudinal axis. That said, the embodiment of FIG. 16 depicts a hybrid device where, for example, the wells located at the distal portions of the electrode array are aligned with the electrodes.

FIG. 17 depicts an alternate embodiment where none of the wells have geometric centers that are aligned with the geometric centers of the electrode arrays, and, as can be seen, there are locations where there are no wells with respect to the respective electrodes. FIG. 17 also presents an exemplary embodiment where a well is located at the tip, as can be seen. In at least some exemplary embodiments, the wells can be located anywhere that can have utilitarian value providing that the structural integrity of the electrode array is not degraded to the point where such frustrates the implantation or otherwise the maintenance of the electrode array in the cochlea.

In an exemplary embodiment, the wells are separated in a manner that maintains a sufficient structural integrity of the electrode array while still providing a utilitarian amounts of therapeutic substance delivery.

FIG. 18 presents an exemplary embodiment where the wells are located every two electrodes. FIG. 19 also presents an exemplary embodiment where the basal portion of the electrode array, or at least a significant section associated with the basal portion (the left side of section 188) do not include wells. The embodiment of FIG. 19 also provides an exemplary arrangement that utilizes different wells at different locations. In this embodiment, the wells that are aligned with the electrodes are short and fat, while the wells that are interleaved between the electrodes are long and thin. While this embodiment depicts the utilization of two separate configurations for wells, in other embodiments, three or four or five or six or seven or eight or nine or 10 or more configurations of wells can be utilized in the same electrode array.

As will be described in greater detail below, the wells can be "filled" with silicone or otherwise can contain bodies of silicone that are impregnated with or otherwise contain a therapeutic substance, from which the therapeutic substance leaves to enter the cochlea (consistent with, in some embodiments, the material above with respect to FIG. 6). In an exemplary embodiment, the therapeutic substance elutes from the wells. Thus, in an exemplary embodiment, there is a carrier of a cochlear implant, and the carrier is made of silicone. The carrier has one or more wells therein, and the one or more wells is/are at least partially filled with a silicone-medicament mixture distinct from the silicone of the carrier, the medicament of the medicament mixture being a therapeutic substance. Additional details of how the "filler" material is provided and the configuration thereof are described below. First however, some geometries of the wells will be described.

Briefly, in view of the above, it can be seen that in an exemplary embodiment, there is a device, such as a cochlear implant electrode array, comprising an electrode array carrier (e.g., 146) and therapeutic substance, such as an anti-inflammatory agent, wherein the therapeutic substance is located in a well of the electrode array carrier. As seen in the embodiments above, in some embodiments, there are a plurality of wells (although in some embodiments, there is only one well) spaced apart from one another along the carrier, the wells of the plurality of wells containing the therapeutic substance. In an exemplary embodiment, there are less than, greater than, or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, or 200 or more wells, or any value or range of values therebetween in increments of one (e.g., 62, 111, 34 to 199, etc.). In an exemplary embodiment, there are less than, greater than or equal to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 110, 120, 130, 140, 150, 160, 170, 180, 190, or 200 or more different well configurations (e.g., the configuration of FIG. 20 versus that of FIG. 8, but in a single array) or any value or range of values therebetween in one increment (e.g., 62, 111, 34 to 199, etc.). These wells can be spaced along the carrier spaced apart from one another. That said, in some embodiments, the wells can be merged with each other.

It is noted and will be described in greater detail below, that a well, void, etc., as disclosed herein, can include a therapeutic substance but also can include other substances. In this regard, the presence of the therapeutic substance does not exclude and/or does not present a carrier that is limited to only having an API/drug mixed with silicone, for example. In this regard, there could also be excipients that are degradable/resorbable, etc., where the actual macro surface area could change because of the well geometry or the excipient dissolving over time. Indeed, some embodiments of such will be described below.

In an exemplary embodiment, with respect to two planes normal to the longitudinal axis of the electrode array from beginning to end of the intracochlear section, spaced apart from one another by 0.05, 0.75, 0.1, 0.15 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 11.0, 12.0, 13.0, 140, 15.0, 16.0, 17.0, 18.0, 19.0, 20.0, 21.0, 22.0, 23.0, 24.0, 25.0, 26.0, 27.0, 28.0, 29.0, 30.0, 31, 32, 33, 34, 35, 36, 37, 38, 39 or 40 mm or any value or range of values therebetween in 0.01 mm increments has less than, greater than or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190 or 200 or more wells or any value or range of values therebetween in one increment (e.g., 62, 111, 34 to 199, etc.). These wells could be spaced linearly without any overlap (in a line, staggered, in an alternating pattern, etc.), with overlap (e.g., as seen in FIG. 14, for example), etc.

Figure 16A:
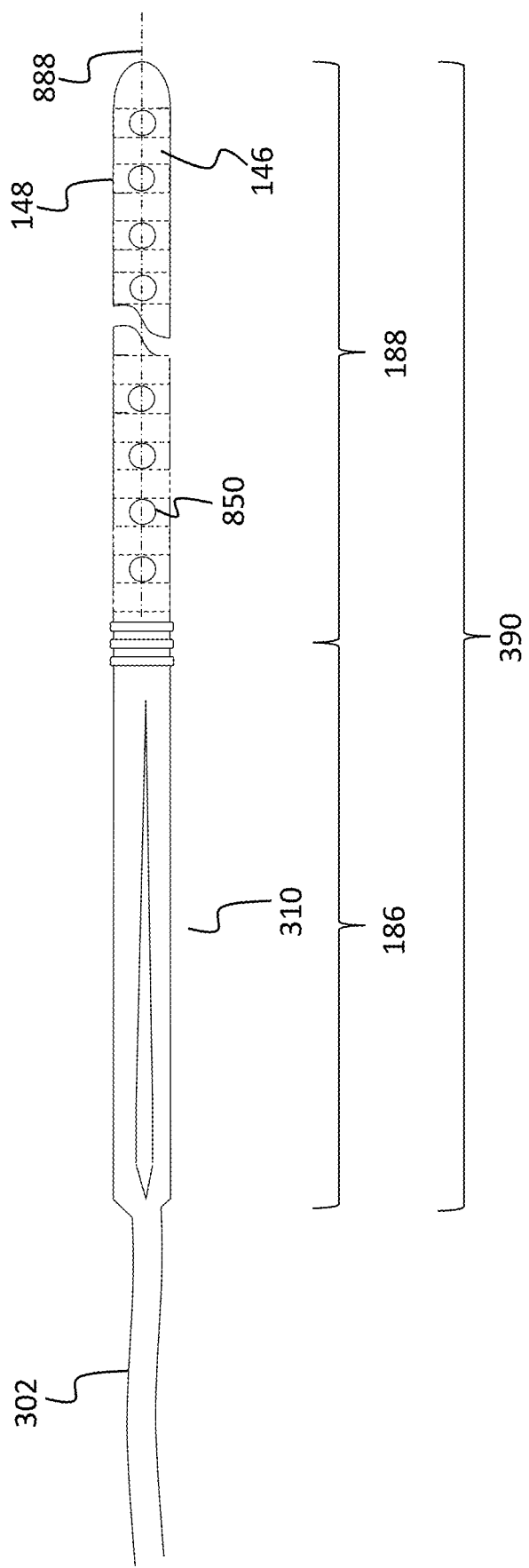

With reference to FIG. 16, it can be seen that there is a longitudinal axis 888 of the carrier section. It can also be seen that none of the wells 850 extend up to that axis 888. In this regard, in an exemplary embodiment, all of the wells are located on one side of the plane extending through the longitudinal axis (e.g., a plane that is normal to the page of FIG. 16 extending through axis 888). This as opposed to an embodiment where there are wells on the electrode side for example (above axis 888). Thus, in at least some embodiments, one or more or all of the wells are spaced apart from one another and at least most of the wells (e.g., 50.1, 55, 60, 65, 70, 75, 80, 85, 90, 91, 92, 93, 94, 95, 96, 97, 98, 99, or 100 percent of the wells (or any value or range of values therebetween in 0.1% increments) are located away from a plane extending through a longitudinal axis of the carrier and electrodes of the carrier. FIG. 16A shows the bottom view of the arrangement of FIG. 16 (looking from the bottom towards to the top of FIG. 16). As can be seen, the wells have circular opening.

Figure 16B:
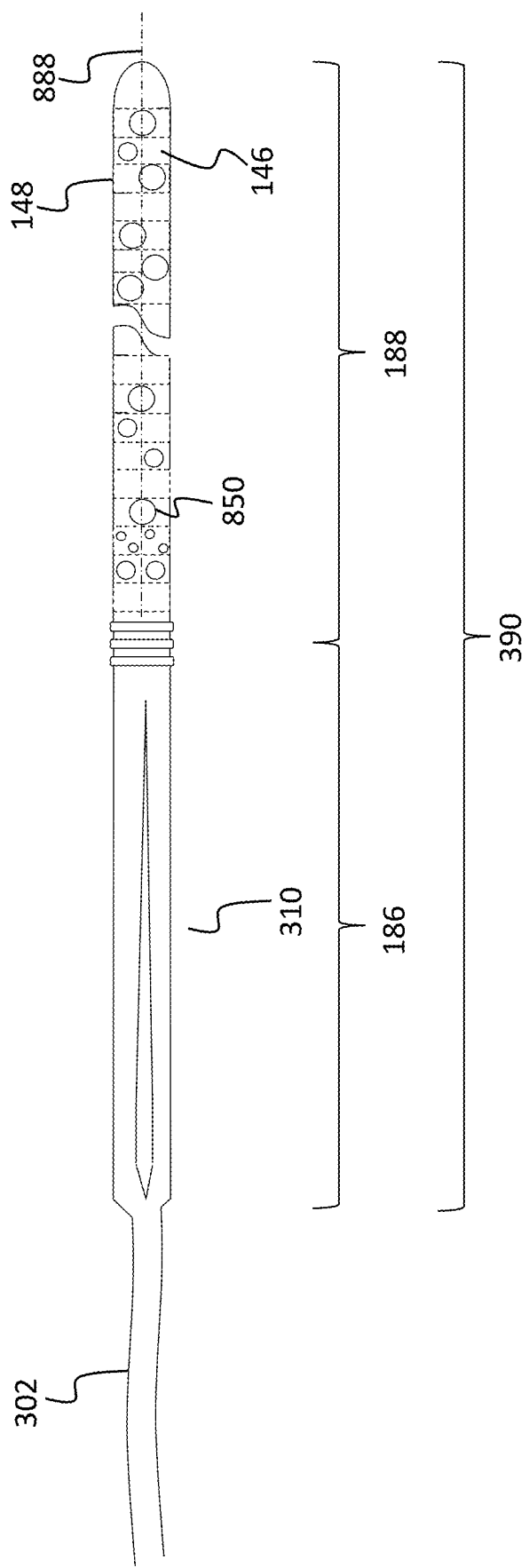

It is noted that in the embodiment shown in FIG. 16, all of the wells are located below the plane that is normal to the page and extends through axis 888. In an embodiment, the wells can be located on one side of the electrode array with respect to the plane that would be parallel to the page of FIG. 16 and extends through the axis 888. FIG. 16B presents another exemplary embodiment with various wells of different sizes located at different locations, as seen.

Figure 27:
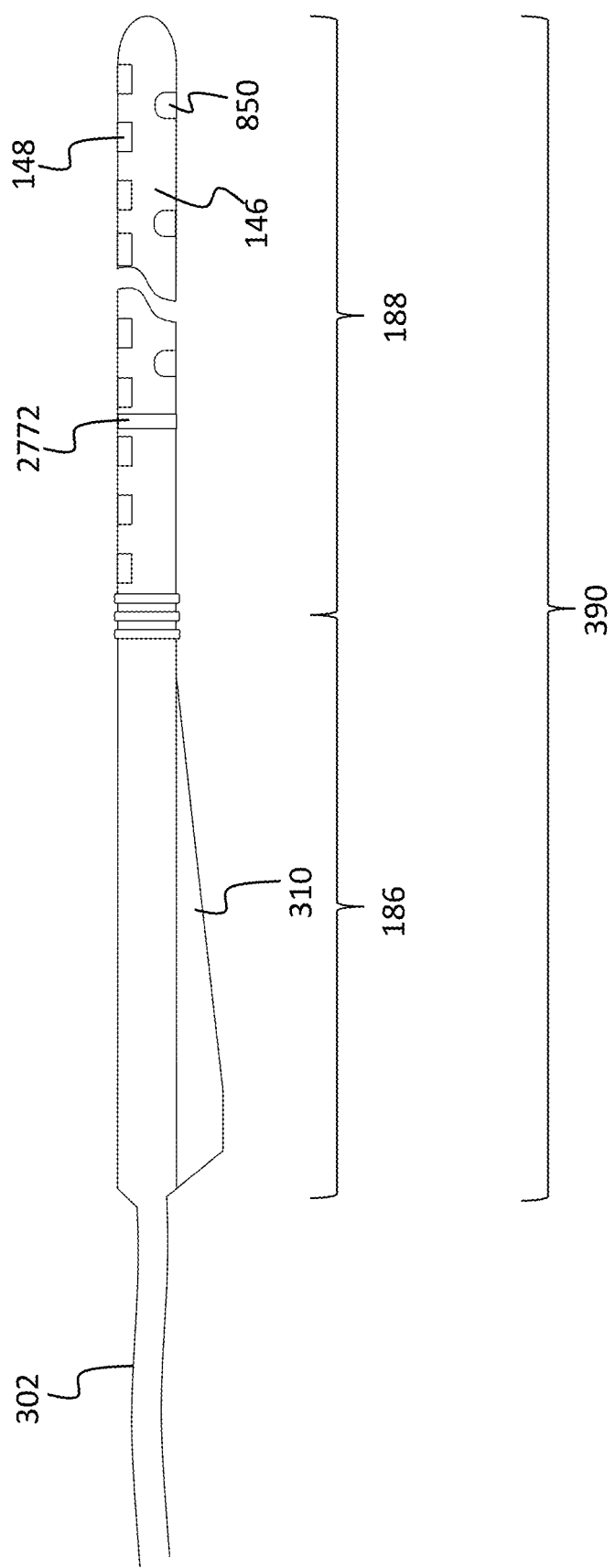

There are other utilitarian features associated with the spatial relationships of the wells. In at least some exemplary embodiments, the cochlear implant electrode array includes a so-called marker, which can be a band that is embedded or otherwise is on the silicone of the carrier, or can be inking or the like or some kind of indicia located on the array. In an exemplary embodiment, the marker extends 360° about the array. This can be seen in FIG. 27 with respect to marker 2772. In an exemplary embodiment, this marker can be utilized as an indicia of a depth of insertion of the carrier into a cochlea during electrode array insertion process into the cochlea. In this regard, for example, because the location of the marker is known relative to the most distal end of the array, the surgeon or the like can ascertain how far the tip has been inserted with respect to how much of the distance of the array between the marker and the hole in the cochlea remains. In an exemplary embodiment, there is no well that is located on the side of the marker opposite a distal tip of the carrier, such as seen in FIG. 27. Alternatively, there can be at least one well that is located on the side of the marker opposite a distal tip of the carrier. In an exemplary embodiment, there are 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, or 200 or more wells, or any value or range of values therebetween in increments of one (e.g., 62, 111, 34 to 199, etc.) on a side of the marker opposite a distal tip of the carrier and/or one the side of the marker that is on a side of the tip of the carrier.

Figure 20:
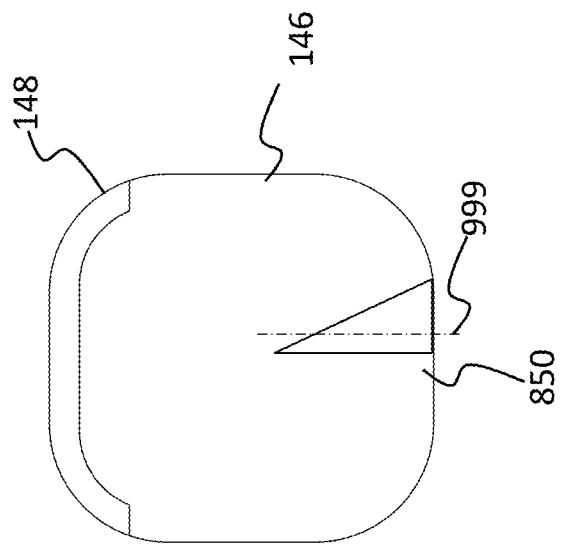

In at least some exemplary embodiments, any well disclosed herein is rotationally symmetric about the longitudinal axis 999 (as seen in FIG. 9 and in comparison to FIG. 8), while in other embodiments, such as seen in FIG. 20, the wells are not rotationally symmetric.

Figure 21:
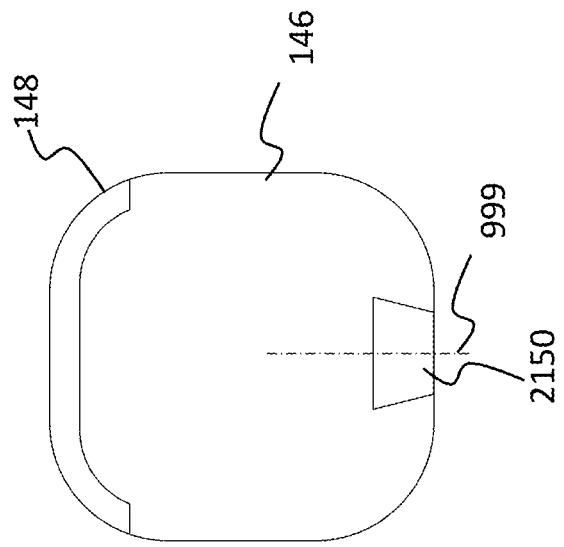
Figure 22:
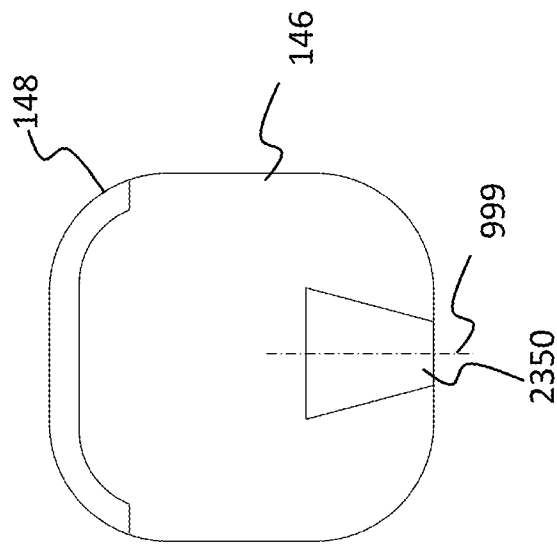
Figure 23:
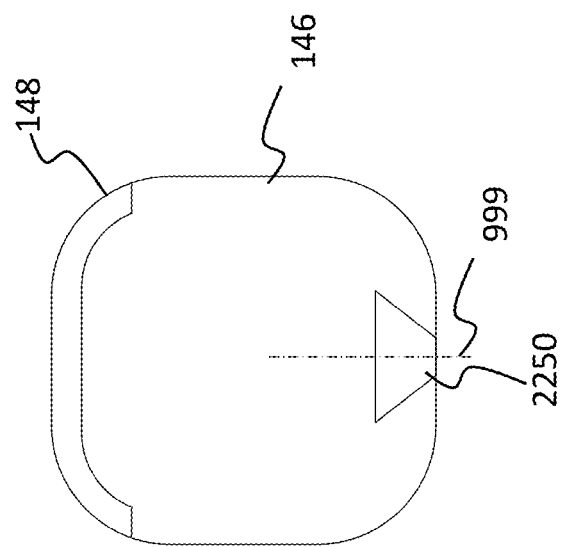

In view of the above, it can be seen that the wells can have a varying cross-section with respect to location along a longitudinal axis thereof (999—the longitudinal axis is the access that extends from the surface of the array from which the well opens). In this regard, as can be seen in FIG. 9, the wells have parallel sidewalls from the opening which end of the wells (bottom), but then the sides of the wells curve inward as seen. In some embodiments, there are no curvatures per se. FIG. 21 represents an exemplary which is trapezoidal, where, with depth (from the bottom of the page to the top of the page of FIG. 21), the well becomes wider. FIG. 22 represents an exemplary embodiment with a well 2250, where the widening (the rate of widening) is more pronounced with depth. FIG. 23 presents an alternate embodiment of a well 2350, where the well has a widening that is less pronounced with that relative to FIG. 22.

Figure 24:
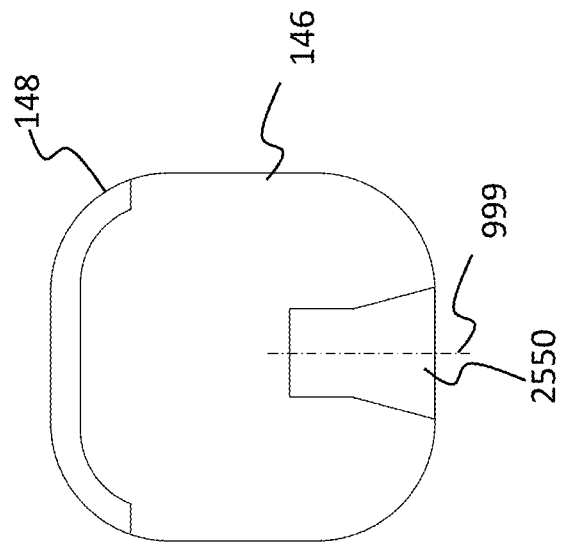
Figure 25:
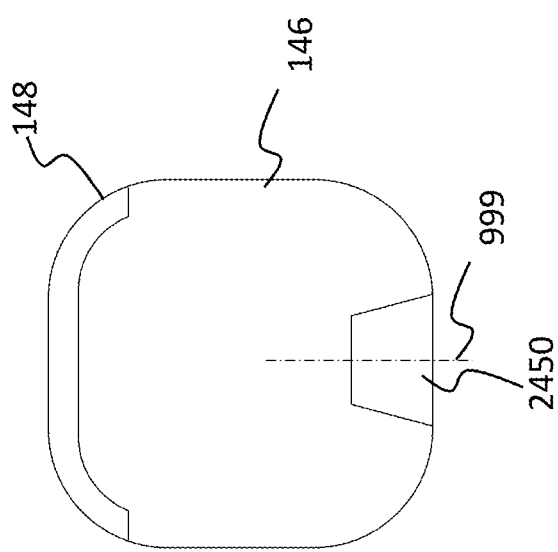
Figure 26:
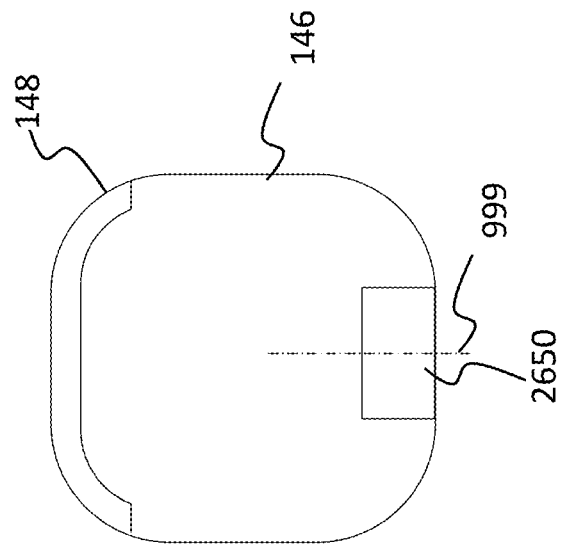

FIG. 24 presents an alternate embodiment of a well 2450, where the well narrows with depth. FIG. 25 presents an exemplary embodiment of a well 2550, where the walls are linear, but there is a narrow ring with depth for first section, and in the width of the well 2550 with depth is constant in the second section. FIG. 26 presents an exemplary embodiment where the width of the well 2650 is constant with depth.

In an exemplary embodiment, the well is deeper than a maximum. In an alternate embodiment, the well has a maximum that is wider than the depth. In an exemplary embodiment, the maximum width is the same as the depth.

In at least some embodiments, one or more or all of the wells are spaced apart from one another and at least most of the wells are located away from a plane extending through a longitudinal axis of the carrier and electrodes of the carrier.

As will be described in greater detail below, in an exemplary embodiment, there are preformed electrode arrays that have a plurality of wells, and, depending on the implementation, some but not all of the wells are provided with therapeutic substance and/or some but not all are fully filled with therapeutic substance and others are only partially filled. Such can provide utilitarian value with respect to developing or otherwise establishing a therapeutic regime for a given recipient relative to another recipient. By way of example only and not by way of limitation, some recipients may require more or less therapeutic substance relative to other recipients, all other things being equal. Accordingly, by having an array that has a plurality of wells, and selectively providing therapeutic substance into only a subset of those wells, the therapeutic substance delivery regimes can be manipulated from recipient to recipient. In an exemplary embodiment, there are a plurality of wells spaced apart from one another (as opposed to at least partially merged). In an exemplary embodiment, a first group of wells numbering between (which is inclusive of) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, or 200 or more or any value or range of values therebetween in 1 increment (e.g., 2 and 10, 5 and 50) have a first general depth and width profile. Further, in this exemplary embodiment, there is a second group of wells numbering between (which is inclusive of) 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 120, 130, 140, 150, 160, 170, 180, 190, or 200 or more or any value or range of values therebetween in 1 increment (e.g., 2 and 10, 7 and 92, etc.) that have a second general depth and width profile different from the first general depth and width profile. There can be a third group, a fourth group, a fifth group, a sixth group, a seventh group, an eighth group, a ninth group, a $10^{th}$, $11^{th}$, $12^{th}$, $13^{th}$ and so on group of wells numbering in accordance with the aforementioned numbering scheme (need not be the same in each group) have an Nth general depth and width profile different from the second general depth and width profile and/or from any one or more or all of the other profiles. In an exemplary embodiment, least one of one or two (or N−1 or any integer within N−1)) of the first, second and third group (or Nth groups) is at least mostly devoid of therapeutic substance (e.g., 50.1, 55, 60, 65, 70, 75, 80, 85, 90, 91, 92, 93, 94, 95, 96, 97, 98, 99 or 100 percent devoid (or any value or range of values therebetween in 0.1% increments)), one or two (or N−1 or any integer within N−1) of the first, second and third group (or of the Nth groups) is at least mostly full of therapeutic substance (e.g., 50.1, 55, 60, 65, 70, 75, 80, 85, 90, 91, 92, 93, 94, 95, 96, 97, 98, 99, or 100 percent (or any value or range of values therebetween in 0.1% increments)), and/or one or two (or N−1 or any integer within N−1)) of the first, second and third group (or Nth group) contains a different therapeutic substance than that contained in one or two of the first, second or third group (or Nth, group or any integer within N).

Thus, at least some exemplary embodiments facilitate multiple drug doses and combination therapies along the array and inside the cochlea.

It is briefly noted that the teachings detailed herein can be applicable to a curly array or a straight array or a semi curved array.

An exemplary embodiment enables a release profile to be varied or otherwise altered or otherwise control over a given period of time with respect to release of the therapeutic substance from a given well. By way of example only and not by way of limitation, as detailed above, the wells can have varying shapes and geometries with respect to cross-section normal to the longitudinal axis of the well. In an exemplary embodiment, it is the surface of the therapeutic substance containing mixture that is exposed to the perilymph of the cochlea that controls or otherwise drives the release rate at a given time. In an exemplary embodiment, an area of 0.1 $mm^2$ of therapeutic substance containing mixture exposed to perilymph letter release rate that is lower than an area of 0.15 mm² of therapeutic substance containing mixture exposed to perilymph. In an exemplary embodiment, over time, the layer that is exposed to the perilymph has an increasing depth relative to the opening of the well. This is because the material above that layer has eluded or otherwise dissolved, or otherwise been removed, over time. By way of example only and not by way of limitation, a well with a depth of 0.3 mm may be charged or otherwise provided with a therapeutic substance that fills the well over the entire depth. In an exemplary embodiment, the well has a circular cross-section with respect to the longitudinal axis of the well (i.e., the width of the well does not change with depth). Respect to the given theft exceptions, it may take 30 days for the therapeutic substance to completely be removed (or effectively completely removed) from the well. In an exemplary embodiment, after 15 days, the surface of the therapeutic substance that is exposed to the perilymph will be located at about the 50% depth level (e.g., 0.15 mm below the opening of the well). This is a linear dissolution profile. In this exemplary embodiment, because the cross-section is constant with depth, the amount of therapeutic substance that will elute on day 10, for example, will be about the same (which includes the same) as the amount that elutes one day 12 or 15 or 20, etc. That said, assuming that there are some features that prevents a linear distribution profile (e.g., the therapeutic substance that remains in a well, the slower the distribution rate, irrespective of the surface area, all other things being equal), surface area will not substantially or effectively or at all impact the elution amount for a given 24 hour period relative to another 24-hour period, at least at temporal locations away from the beginning and the end of the elution period (e.g., 6, 12, 18, 24, 30, 36, 48 hours or 3 or 4 or 5 days after the beginning of the period and/or before the end of the period, where other drivers may take place). This is because, in this exemplary embodiment, the surface area that is exposed to perilymph is constant.

Figure 28:
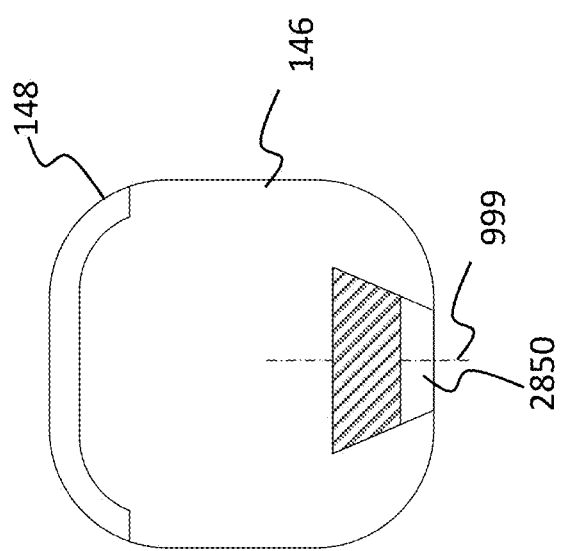
FIGS. 28 and 29 and 30 and 32 and 36 and 37 and 38 and 40 and 42 and 43 and 41 and 39 and 45 and 46 and 52 present views looking down the longitudinal axis of some arrays according to some exemplary embodiments.
Figure 29:
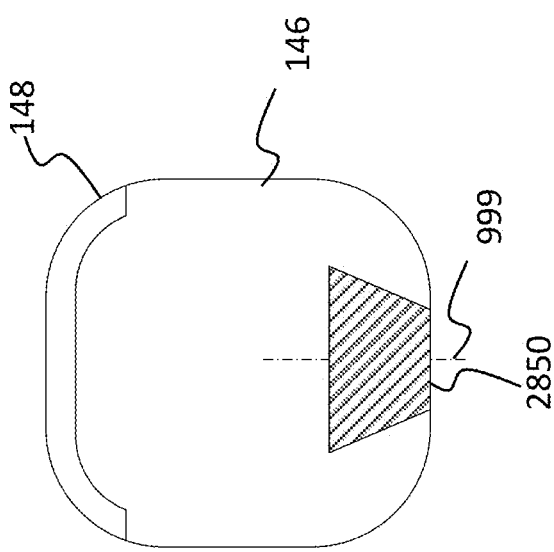
Figure 30:
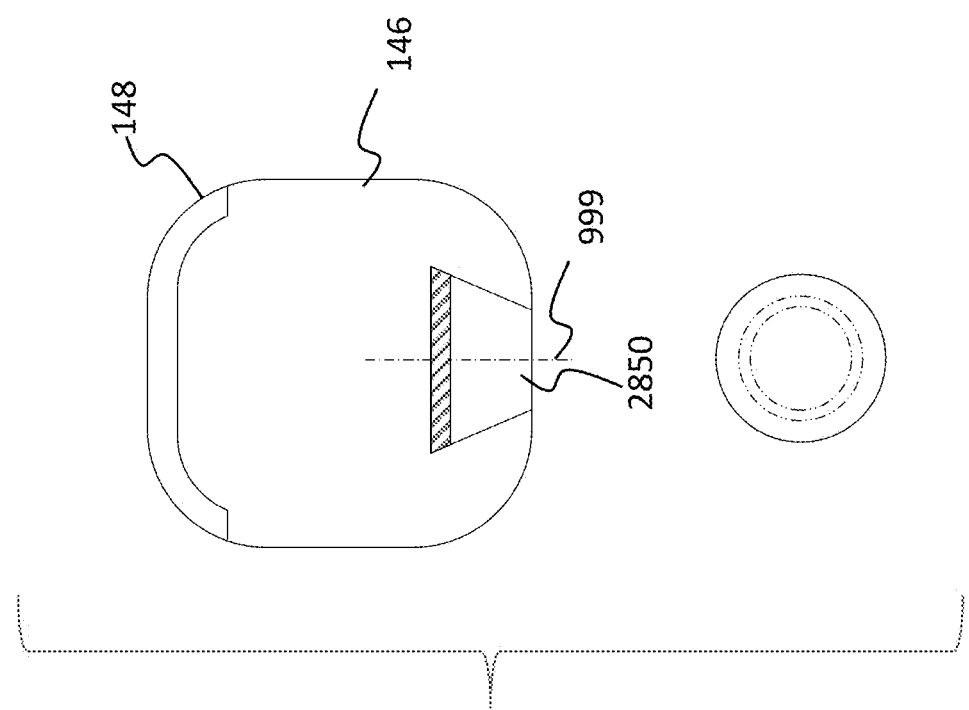

Conversely, the surface area that is exposed to perilymph with respect to a well that has a varying cross-section will change over time with the amount of therapeutic substance that elutes, thus lowering the level of therapeutic substance that is exposed to the perilymph. Briefly, by way of schematic representation example only and not by way of limitation, FIGS. 28-30 illustrates this concept by way of conception. At time zero, which could be any of the aforementioned times after implantation into the cochlea and/or after exposure to the therapeutic substance of perilymph, the well 2850, which is a trapezoidal well, is full of therapeutic substance containing material. The therapeutic substances represented by the crosshatching. The circle at the bottom of the FIG. 28 represents the surface area of the therapeutic substance that is directly exposed to the perilymph at time zero. FIG. 29 represents time T1 after time zero, which could be, for example, 10 days. As seen, at least some of the therapeutic substance has eluted or otherwise dissolved into the perilymph and thus into the cochlea. The material containing the therapeutic substance may or may not be present. The point is, the area above the surface level (between the crosshatching and the opening of the well) is now for the most part at least devoid at least effectively of therapeutic substance contained in the material. The crosshatching represents the remaining therapeutic substance. The circles below in FIG. 29 represent the difference in the cross-sectional area that represents the top layer of therapeutic substance that is now exposed to the perilymph. As can be seen, the area is now larger, owing to the fact that well 2850 widens with depth. In an exemplary embodiment, the elution rate at time T1 will be greater than that which was the case at time T0, owing to this larger area. The difference in the rate can be proportional to the area change.

FIG. 30 represents time T2 after time zero, which could be, for example, 20 days or 25 days. As seen, more of the therapeutic substance has eluted or otherwise dissolved into the perilymph and thus into the cochlea relative to that which was the case at T1. The material containing the therapeutic substance may or may not be present. Again, the point is, the area above the surface level (between the crosshatching and the opening of the well) is now for the most part at least devoid at least effectively of therapeutic substance contained in the material. The crosshatching represents the remaining therapeutic substance. The circles below in FIG. 30 represent the difference in the cross-sectional area that represents the top layer of therapeutic substance that is now exposed to the perilymph. As can be seen, the area is now larger than that which was the case in either of FIGS. 29 and 28, owing to the fact that well 2850 widens with depth. In an exemplary embodiment, the elution rate at time T2 will be greater than that which was the case at time zero and T1, owing to this larger area. The difference in the rate can again be proportional to the area change.

It is to be understood that this concept can operate in reverse, such as with respect to the embodiments detailed above where the cross-sectional area narrows with depth. It is to also be understood that this concept operates in a manner that can enable the elution rate to have a first or second or third rate and then maintain a given rate during a later period of time, such as, for example, utilizing a well that has a constant cross-section at a greater depth.

It is briefly noted that in at least some exemplary embodiments, the utilizations of different widths can be utilized to achieve a potentially constant elution rate. In this regard, in some exemplary embodiments, as the overall amount of therapeutic substance is reduced, the elution rate could change even with a constant diameter well. This can be a function of the material that contains the therapeutic substance. Accordingly, by varying the width of the well, it can be possible to maintain the rate to otherwise account for this change that is linked to the overall amount.

Still, in at least some exemplary embodiments, the change in cross-sectional area of the well is utilized to change the rate of elution (which is included in "control" the rate of elution).

Figure 31:
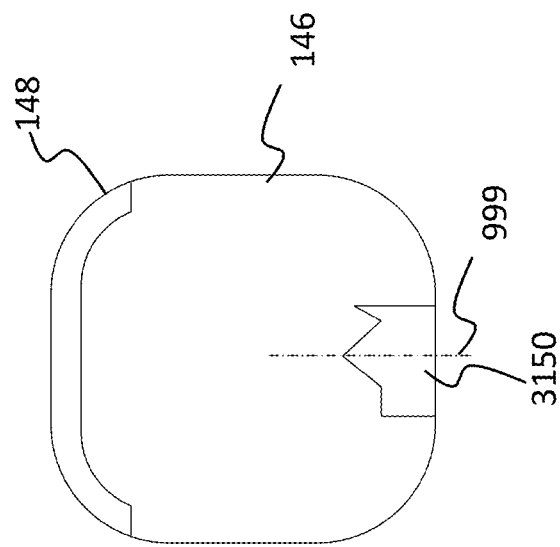
Figure 32:
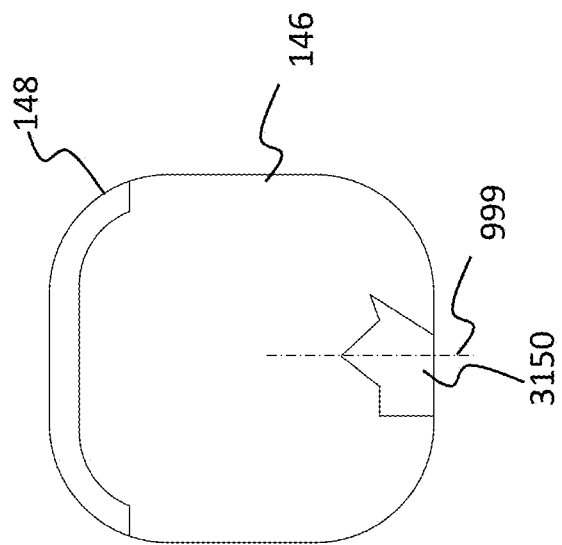

FIG. 31 provides another exemplary well 3150, according to an exemplary embodiment. As can be seen, the well has a plurality of depths/has a nonuniform depth. By varying the depths of portions of the well, the elution rates can be varied in at least some exemplary embodiments. FIG. 32 presents an exemplary embodiment where the well 3250 has different depths and has different widths (over all of the longitudinal length of the well). It can be seen that in this exemplary embodiment, the release rate can be ramped up, and then ramped down. Moreover, in an exemplary embodiment, the release rate can be ramped up, then ramped down, and then ramped up again and then ramped down, all with time.

In view of the above, in an exemplary embodiment, there is a device, such as for example and not by way of limitation, a cochlear implant electrode array, what in alternate embodiments, for example, a retinal implant electrode array, or a spine stimulator or a pacemaker, etc., comprising an electrode array carrier and a therapeutic substance. In an exemplary embodiment, the therapeutic substance is located in at least one cavity of the carrier (e.g., a well, but this is not so limited to such—as will be detailed below, some embodiments can be used with a backstrap configuration, etc.), the cavity having at least one of a non-uniform depth or a non-uniform width with respect to location in a direction of the depth that has an effective impact on a delivery of the therapeutic substance to a human. In an exemplary embodiment, the cavity has the non-uniform width with respect to the location in the direction of the depth but not the non-uniform depth, while in other embodiments, it has the non-uniform depth but not the non-uniform width, while in other embodiments, it has both.

Figure 33:
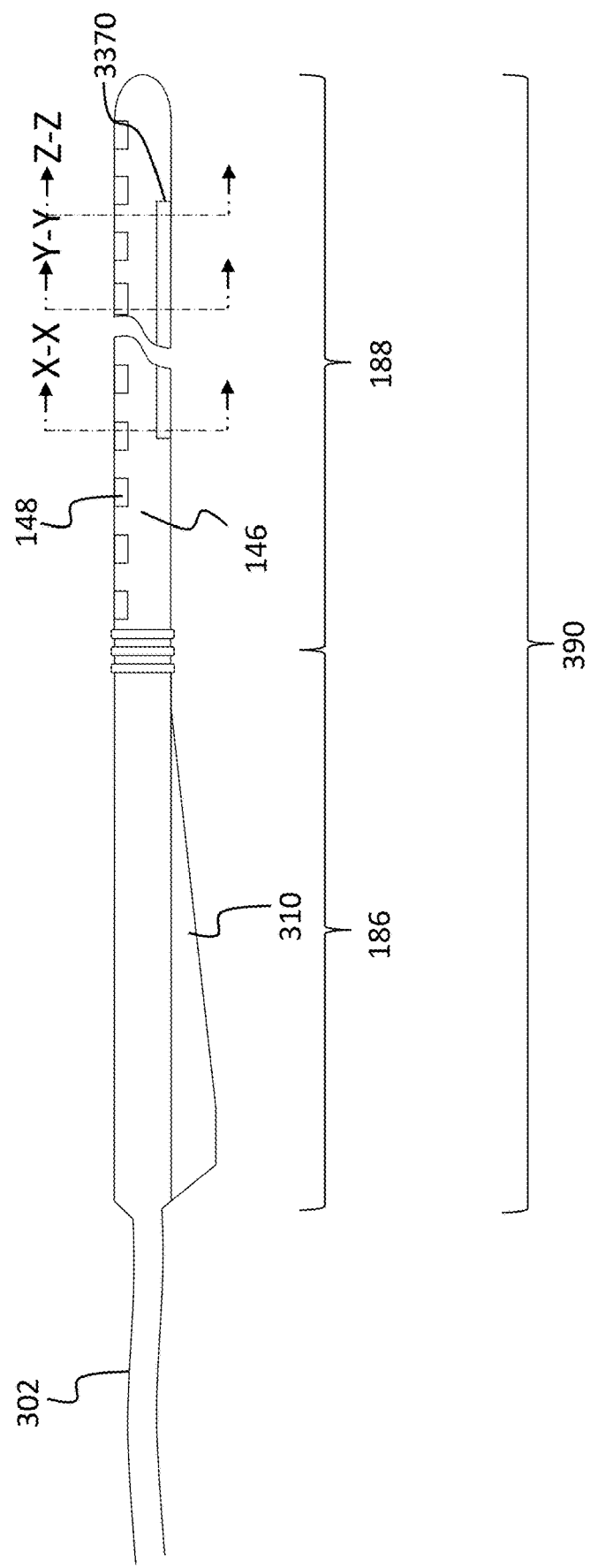
FIGS. 33-35 present side views of exemplary embodiments of exemplary electrode array assemblies.

In an exemplary embodiment, the cavity is a well extending from the outer surface of the carrier, in accordance with FIGS. 8-32. Conversely, the cavity is not a well in other embodiments. In this regard, in an exemplary embodiment, the cavity has an elongate portion that extends in a longitudinal direction of the carrier. By way of example only and not by way of limitation, the cavity can be the cavity of a backstrap, such as seen in FIG. 33, and thus the material therein can be a backstrap like body. That said, in some embodiments, the elongate portion is not so long as to establish a cavity for a backstrap.

Figure 34:
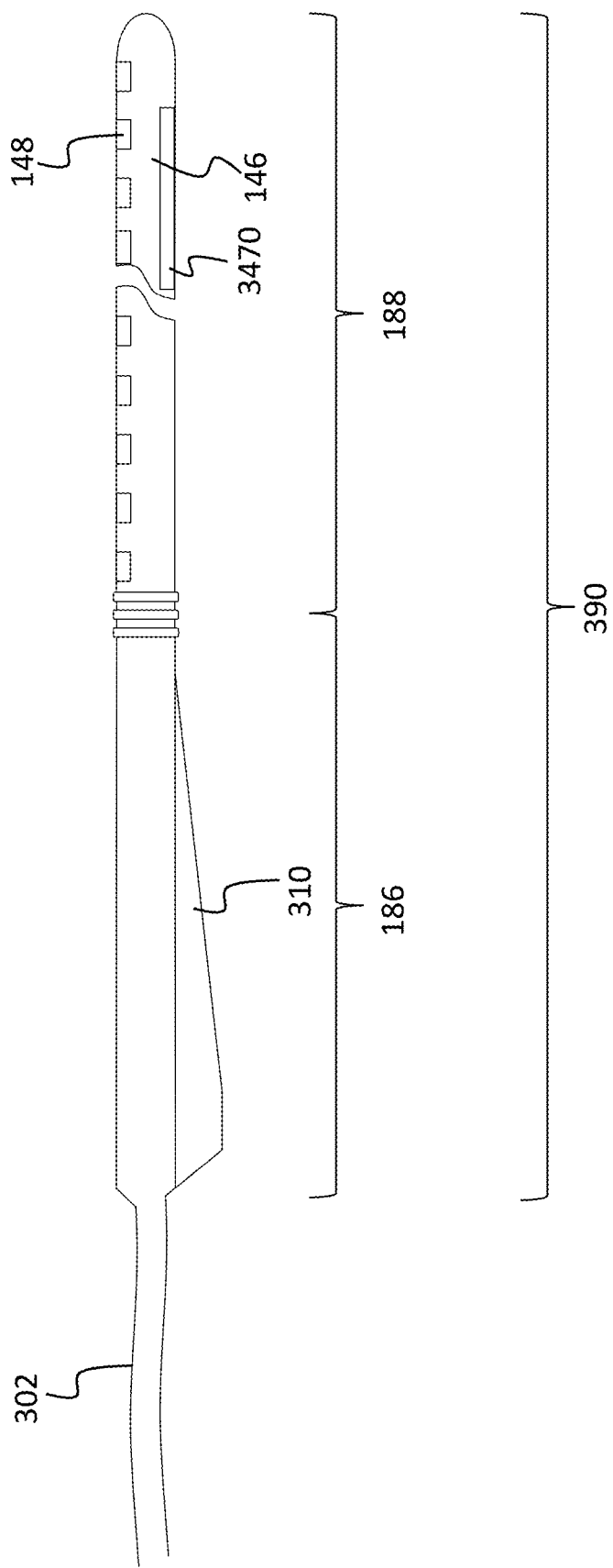
Figure 35:
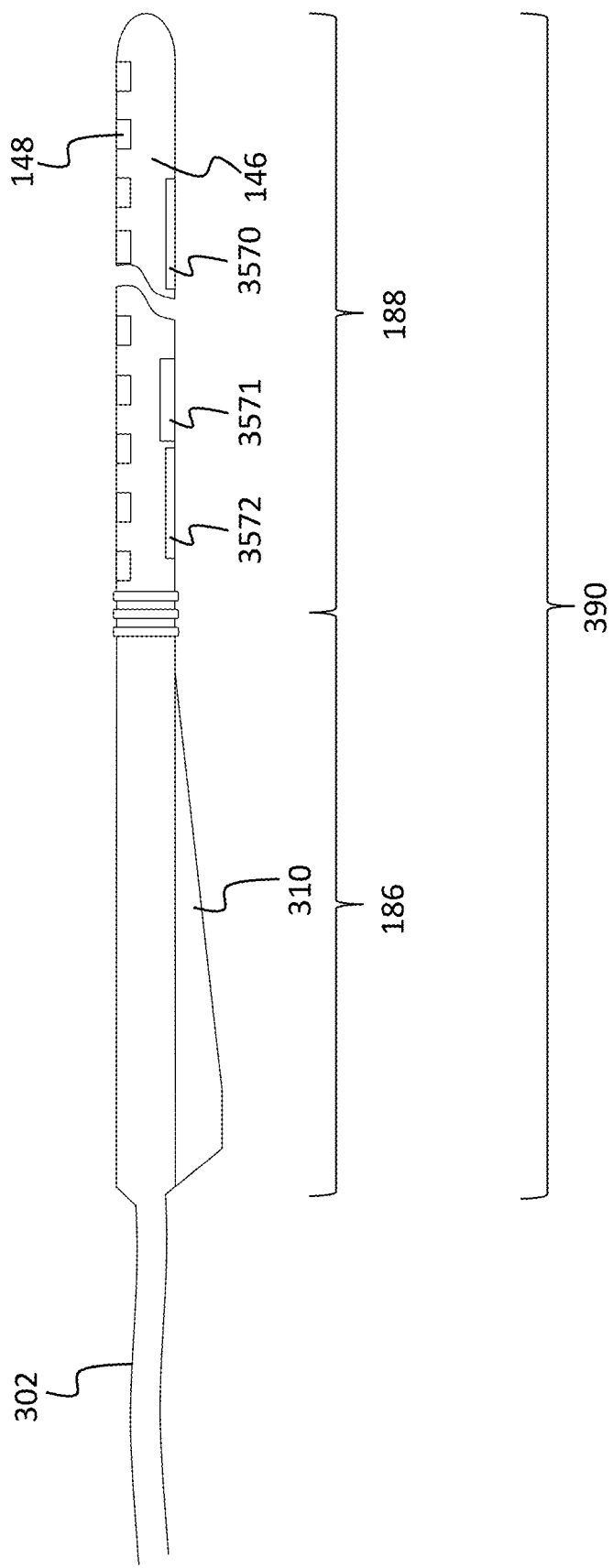

In some embodiments, the device is devoid of a backstrap and/or a tip containing a therapeutic substance, and thus a cavity(s) for such. Conversely, in other embodiments, there is a backstrap and/or a tip containing the therapeutic substance, and there are also cavitie(s) for such. In some embodiments, in addition to those cavities for the backstrap (s) and/or for the tip, there are wells. FIGS. 33 and 34 and 35 depict cross-sections of non-well cavities 3370 and 3470 and 3570 and 3571 and 3572, where the cross-sections looking down the length of the longitudinal axis correspond to FIG. 24, for example. In an exemplary embodiment, there are at least Z cavities having the at least one of a non-uniform depth or a non-uniform width with respect to location in a direction of the depth, where Z is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100 or more or any value or range of values therebetween in 1 increment.

In an exemplary embodiment, there is a device, comprising an electrode array carrier, and a therapeutic substance, wherein at least one of (i) the electrode array carrier and the therapeutic substance are collectively arranged to provide for a therapeutic substance release rate that is variable over time or (ii) the therapeutic substance is located in a plurality of wells that are spaced apart from one another, at least some of the wells being located in pairs at a same distance along a longitudinal axis of the carrier. In an exemplary embodiment where the electrode array carrier and the therapeutic substance are collectively arranged to provide for a therapeutic substance release rate that is variable over time, the rate can vary owing to the different geometries of the well(s). In an exemplary embodiment, over a period of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100 hours and/or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100 days or more, or any value or range of values in 1 minute increments from a point in time at or after implantation, where the point in time can be from the time that the array is fully inserted into the cochlea, all electrodes are in the cochlea, no more repositioning of the array occurs, the surgical opening to implant the implant is fully closed (last suture/staple, or whatever they use has been put in place), etc., and the time from the point in time can be 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes or hours 0.25, 0.5, 0.75, 1, 2, 3, 4, 5, 6, 7, 8, 9, 10 days or any value or range of values in 6 second increments from the point in time, the rate of elution (mass and/or volume, per second, per minute, per 1, 2, 3, 4, 5, 6, 7, 8, 9, 10, 11, 12, 13, 14, 15, 20, 25, 30, 35, 40, 45, 50, 55, 60 minutes or any value or range of values therebetween in 1 second increments, or per 0.1, 0.2, 0.3, 0.4, 0.5, 0.6, 0.7, 0.8, 0.9, 1, 1.25, 1.5, 1.75, 2, 2.25, 2.5, 2.75, 3, 3.5, 4, 4.5, 5, 5.5, 6, 6.5, 7, 7.5, 8, 9, 10, 11, 12, 13, 14, 15, 16, 17, 18, 19, 20, 21, 22, 23, 24, 25, 26, 27, 28, 29 or 30 hours or any value or range of values therebetween in 1 minute increments) from one or more or all or less than, greater than or equal to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99 or 100% of the cavities or wells of the array or any value or range of values therebetween in 0.1% increments that are located inside the cochlea and/or exposed to body fluids can vary by H amount 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99 or 100 times or more or any value or range of values therebetween in 1 increment). In an exemplary embodiment, H is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99, 100, 110, 120, 130, 140, 150, 160, 170, 180, 190, 200, 225, 250, 275, 300, 350, 375, 400, 450, 475, 500, 525, 550, 575, 600, 650, 700, 750, 800, 850, 900, 950, 1000, 1250, 1500, 1750, 2000, 2500, 3000, 3500, 4000, 5000, 6000, 7000, 8000, 9000, or 10000% or any value or range of values therebetween in 0.1% increments, positive or negative (the negative being with respect to the 100% and lower values) relative to one or more of the prior rate immediately before the change, such, as for, example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99, 100 or more rate changes or any value or range of values therebetween in 1 increments before the rate change at issue.

Figure 37:
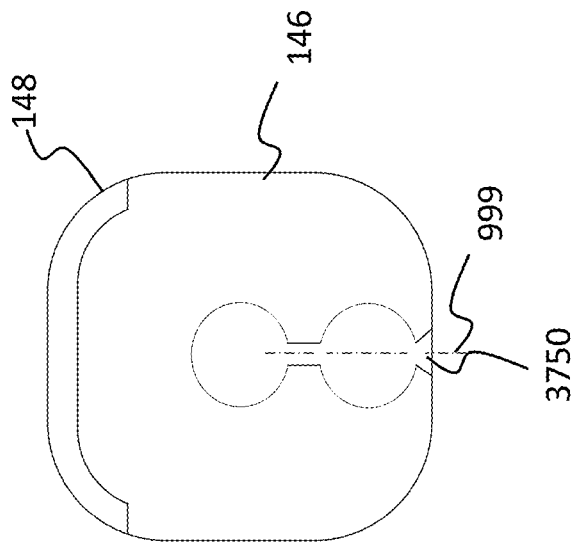
Figure 36:
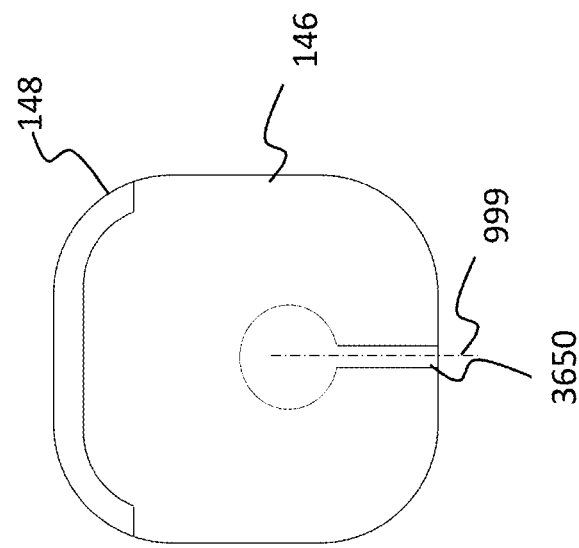

In an exemplary embodiment, the wells and/or cavities can be "aggressively" configured to provide a large rate of change at a given time. By way of example only and not by way of limitation, FIG. 36 presents an exemplary well, well 3650, which has a relatively narrow section which leads to a relatively wide section. Here, the amount of elution of therapeutic substance during a first time is relatively low until the substance elutes to the level of the large section, at which point the rate of therapeutic delivery will increase dramatically relative to that which was previously the case. It is also be understood that in an alternate embodiment, the opposite can be the case: the high rate of elution can occur followed by a relatively lower rate. Further, the arrangement can be combined such that a high rate exists in a low rate exists and then a high rate exists, etc. FIG. 37 presents an example of this with respect to well 3750.

Figure 38:
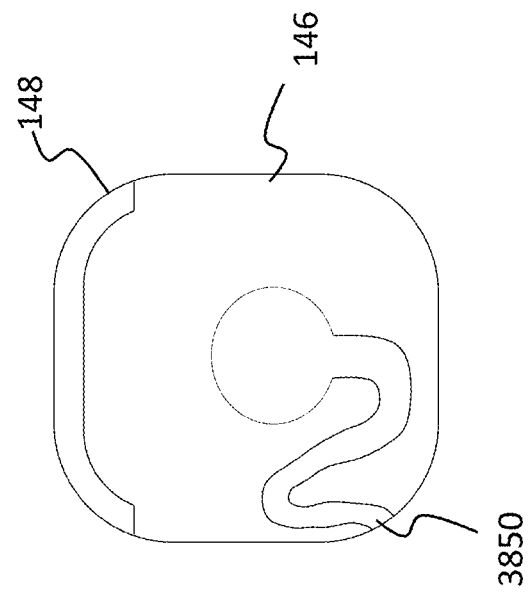

It is noted that in some embodiments, to achieve a significantly temporally delayed increase in release, the well can be configured to wind and/or snake within the electrode array carrier to "buy time" for the released rate to increase. FIG. 38 presents such an exemplary embodiment with respect to well 3850.

It is to be understood that with respect to embodiments where the therapeutic substance is presented in generally uniform concentrations per unit volume within the well, the therapeutic substance will be eluting while the therapeutic substance is exposed to the body fluids. Thus, there can be times when there is some amount of therapeutic substance that is being delivered into the perilymph, for example, however low rate that might be. In an exemplary embodiment, a "composite charge" can be used. In an exemplary embodiment, the substance that initially elutes can be an inert ingredient or a non-active ingredient or nonactive substance, where, until that material or substance fully or effectively fully elutes to expose the therapeutic substance that is "behind" the nonactive ingredient, the therapeutic substance or no therapeutic substance is being delivered to the cochlea. Then, when that nonactive ingredient has effectively fully eluted, thus exposing the therapeutic substance, the released rate will substantially increase. This arrangement can be utilized in combination with the wells detailed herein. By way of example only and not by way of limitation, with respect to FIG. 36, the narrow portion of the well can be partially and/or fully loaded with a nonactive ingredient, while the wider area of the well can be filled with an active ingredient. That said, the wider area of the well can be partially or fully loaded with a nonactive ingredient. Indeed, in an exemplary embodiment, such as where a release of the therapeutic substance is not desired over an and the period of time, the bottom of the well could be loaded with this nonactive ingredient. That said, in an exemplary embodiment, the bottom of the well can be loaded with a substance that does not elute and will not take or absorb any therapeutic substance or active ingredient. By analogy, this is can be akin to placing rocks or stones into the bottom of a drinking glass to displace the fluid in the glass.

Figure 40:
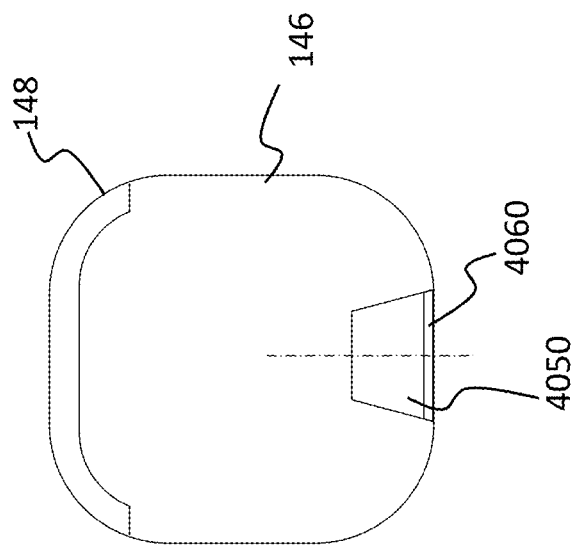

Embodiments can be configured so that there is a covering or the like over a given well. By way of example only and not by way of limitation, FIG. 40 depicts well 4050, which is covered by a layer of silicone 4060. In an exemplary embodiment, the silicone layer 4060 is not impregnated or otherwise charged with a therapeutic substance or an active ingredient. However, the therapeutic substance can elute through the layer 4060. In at least some exemplary embodiments, by changing the thickness and/or porosity and/or the nature of the silicone layer 4060, the time at which the elution of the therapeutic substance will begin to occur and/or the rate of elution once the elution begins to occur can be varied. Thus, in an exemplary embodiment, there can be a layer of silicone that is located over the therapeutic substance. Also, in some embodiments, there are wells that have the layer of silicone and others that do not have a layer of silicone. Accordingly, in at least some exemplary embodiments, there is a layer of silicone is located over the therapeutic substance at some locations and not at other locations.

In an exemplary embodiment, there is an electrode array carrier that includes a well in which the therapeutic substance is located and the well has a geometry such that the therapeutic substance therein has an XYZ state release profile owing to the geometry, where XYZ can be 1, 2, 3, 4, 5, 6, 7, 8, 9, 10, 11, 12, 13, 14 or 15 or more.

In an exemplary embodiment, the silicone layer that is provided can slow the released rate so that the rate is at least 5, 10, 15, 20, 25, 30, 35, 40, 45, 50, 55, 60, 65, 70, 75, 80, 85, or 90% or more, or any value or range of values therebetween in 1% increments relative to that which would be the case in the absence of the layer, all other things being equal and/or the time that the therapeutic substance begins to be released by at least 0.2, 0.4, 0.6, 0.8, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours or days, or any value or range of values therebetween in 1 minute increments In an exemplary embodiment, the geometry differences of a well can enable 1, 2, 3, 4, 5, 6, 7, 8, 9, 10, 11, 12, 13, 14, 15, 16, 17, 18, 19, or 20 different effective rate changes. In an exemplary embodiment, the geometry differences of a well can enable 1, 2, 3, 4, 5, 6, 7, 8, 9, 10, 11, 12, 13, 14, 15, 16, 17, 18, 19, or 20 different rate changes that meet a minimum rate change of any of the above noted percentages.

In an exemplary embodiment where the electrode array carrier includes a well in which the therapeutic substance is located, the well has a cross-section lying on a plane that is normal to a longitudinal axis of the carrier, such that the well at least one of widens or narrows with location closer to the longitudinal axis. In an exemplary embodiment where the electrode array carrier includes a well in which the therapeutic substance is located, the well has a plurality of cross-sections lying on respective first planes are normal to a second plane that is normal to a longitudinal axis of the carrier, such that the area of the cross-section at least one of increases or decreases with location closer to the longitudinal axis. In an exemplary embodiment, the above-noted widening and/or narrowing and/or increasing and/or decreasing may not be constant. In an exemplary embodiment, the rate of widening and/or narrowing and/or increasing or decreasing may change with location, where the rate is measured from a previous location. In an exemplary embodiment, the rates can also change from positive to negative. Thus, in an exemplary embodiment, an area of the cross-section can widen from a first location to a second location, and then narrow from the second location to a third location. Moreover, in at least some exemplary embodiments, the widths in the areas can be constant from a given location to another location. In an exemplary embodiments, there can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 80, 90, 100, 110, 120, 130, 140, 150, 160, 170, 180, 190 or 200 or 250 or 300 or more or any value or range of values therebetween in one increments separated by a distance of 0.05, 0.075, 0.1, 0.15 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.00 mm or any value or range of values therebetween in 0.001 mm increments. The distance can be measured along an axis of depth of the well. This can be a compound axis, such as that which would result in FIG. 38, for example, where the axis would snake along the well from the opening of the well to the center of the large volume. Also, the above noted distances can instead be measured with respect to distance along the axis, and the areas being with respect to planes that are normal to the axis of depth, and the plane upon which the width is measured can be a plane that is normal to a plane that is normal to the axis of depth.

In an exemplary embodiment, there is an electrode array carrier that includes a void extending along a longitudinal axis opening to a lateral side of the electrode array carrier, and the therapeutic substance is located in the void in the form of a backstrap. In this regard, the void can have a cross-section according to any of those detailed herein, or any other of those detailed herein, wherein, by way of example only and not by way of limitation, the width and/or the depth can vary according to any of the teachings detailed herein or variations thereof, which cross-section can be at different sections along the longitudinal axis of the electrode array, and wherein the cross-sections are present on planes that are normal to the longitudinal axis of the electrode array. In an exemplary embodiment, the cross-section is constant for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99, or 100 percent, or any value or range of values therebetween in 0.1% increments along the length of the void. In an exemplary embodiment, there can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99, or 100 or more, or any value or range of values therebetween in one increment distinctly different cross-sections when measured on respective planes that are normal to the longitudinal axis of the electrode array at the above noted distances vis-à-vis the cross-sections with respect to the well detailed above.

Figure 43:
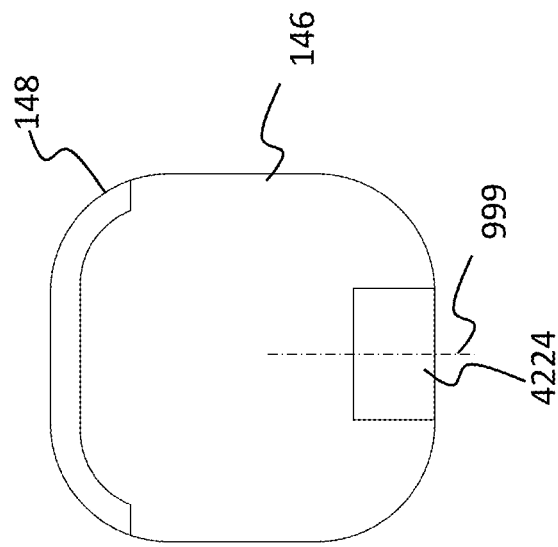
Figure 42:
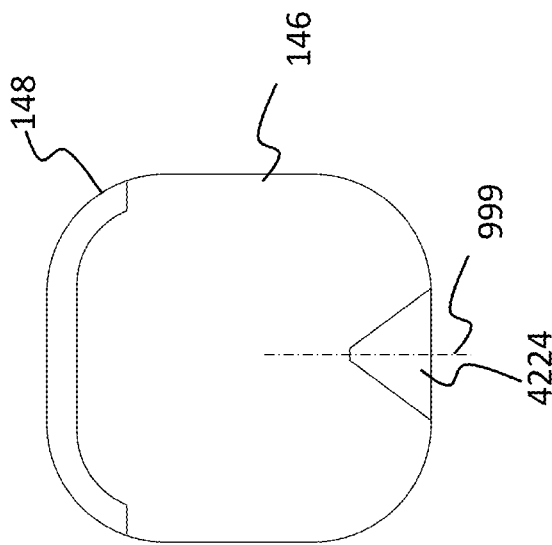

With respect to FIG. 33, which indicates there are three cross-sections taken through the carrier, in an exemplary embodiment, cross-section X-X, Y-Y and Z-Z can be the same, and could correspond to, for example, FIG. 24, or any other cross-section for this matter. In this regard, the cross-section is constant along the length of the backstrap, and/or the void/cavity (any disclosure herein with regard to the material of the therapeutic substance corresponds to a disclosure of an embodiment of the void containing such, and vis-a-versa, unless otherwise noted). That said, in an alternate embodiment, the cross-sections can change along the length. In this regard, X-X or Y-Y and/or Z-Z can correspond to, for example, that of FIG. 24, and another one can correspond to, for example, that of FIG. 42, which has strap 4224 (which is a continuation of the strap of FIG. 24, for example), and another one can correspond to, for example, that of FIG. 43, which has strap 4334, which is also a continuation of the strap.

Figure 44:
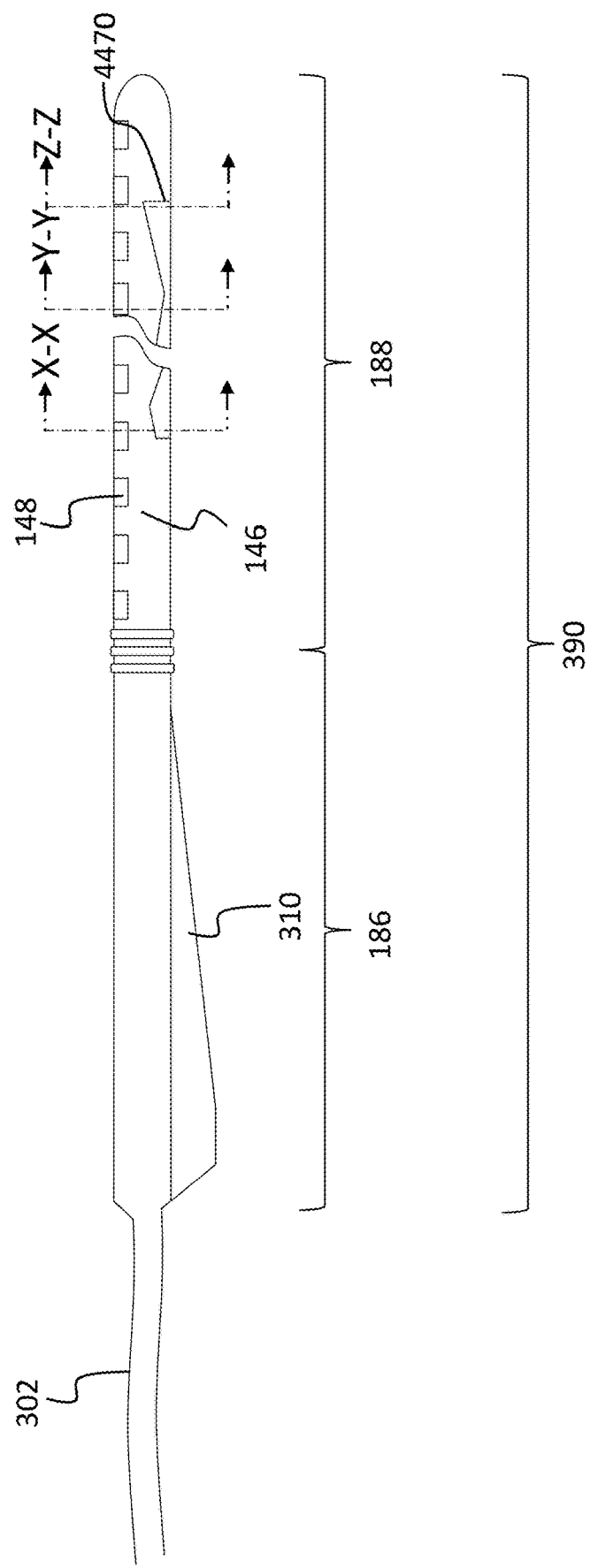
FIG. 44 presents a side view of exemplary embodiments of exemplary electrode array assemblies.
Figure 46:
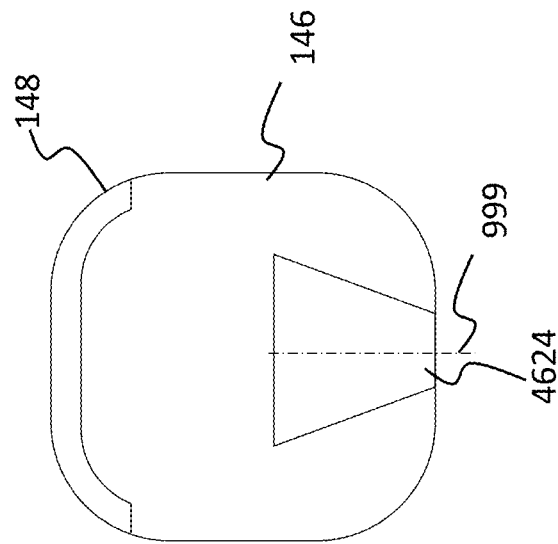
Figure 45:
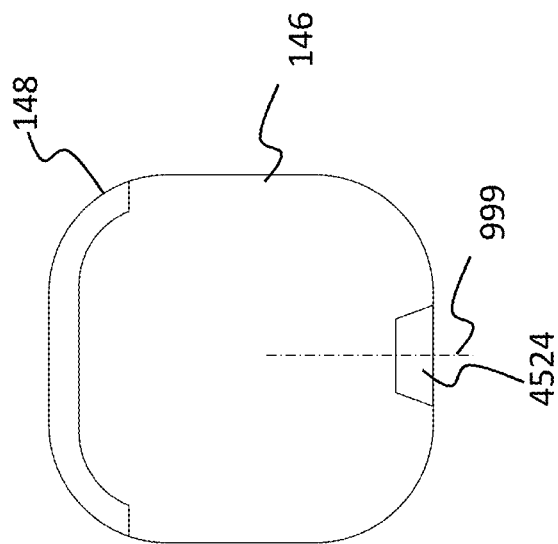
Figure 47:
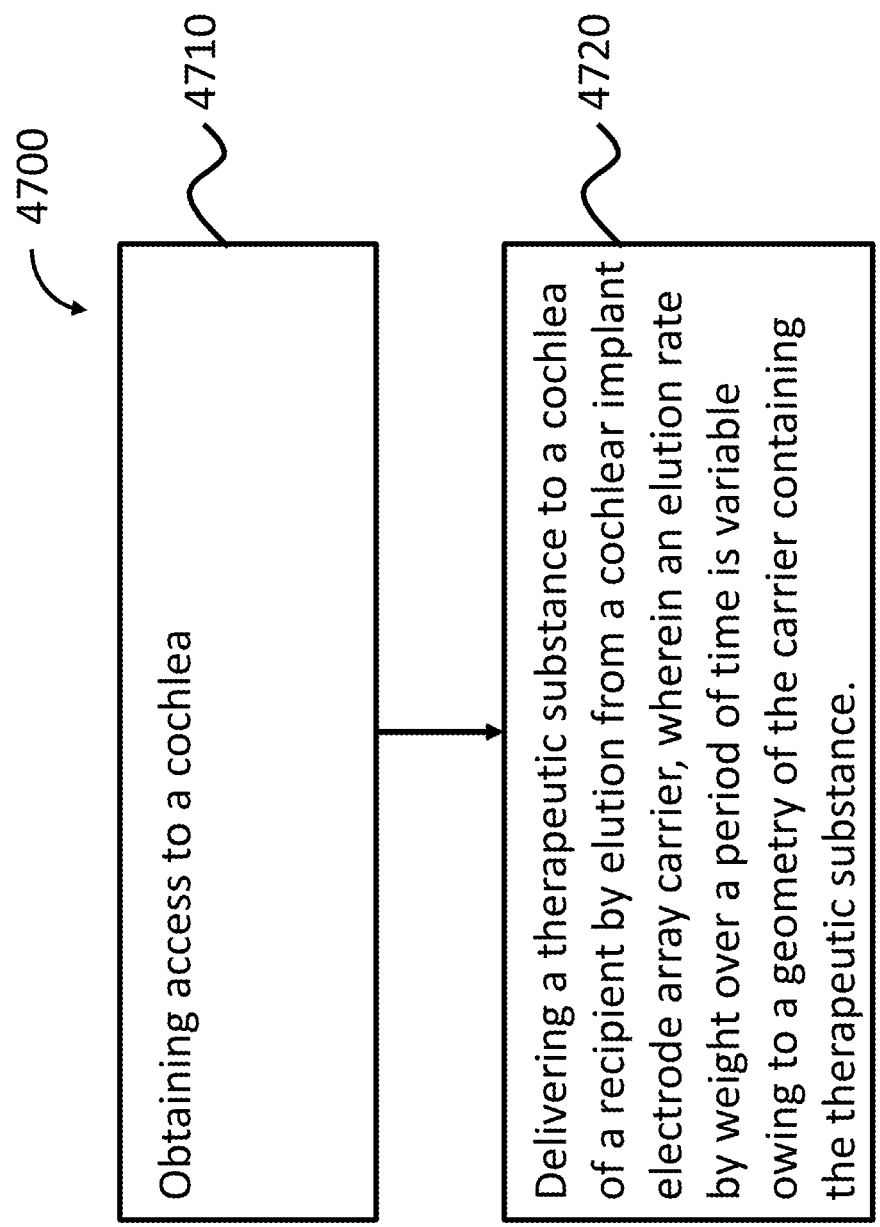
FIGS. 47 and 48 and 49 present exemplary flowcharts for exemplary method embodiments.

FIG. 44 presents an alternate exemplary embodiment of a backstrap 4470/void 4470, where the depth of the void varies along the length of the backstrap. In an exemplary embodiment, cross-section X-X can correspond to that of FIG. 24, cross-section Y-Y can correspond to that of FIG. 45, for example, and cross-section Z-Z can correspond to that of FIG. 46 by way of example. Again, the geometries can vary widely according to any geometry that can have utilitarian value. These examples are for conceptual purposes to illustrate the underlying teachings of at least some exemplary embodiments.

In an exemplary embodiment, the devices can be devoid of glue holding the therapeutic substance and/or the therapeutic substance is a drug that is mixed in a silicone separate from the electrode array carrier. In an exemplary embodiment, the therapeutic substance is located in a plurality of wells that are spaced apart from one another, at least some of the wells being located in pairs at a same distance along a longitudinal axis of the carrier. In an exemplary embodiment, the therapeutic substance is located in a plurality of wells that are spaced apart from one another, at least some of the wells being located in pairs at a same distance along a longitudinal axis of the carrier and spaced away from a plane that extends through electrodes and the longitudinal axis of the carrier. In an exemplary embodiment, there are at least 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 91, 92, 93, 94, 95, 96, 97, 98, 99, 100, 110, 120, 130, 140, 150, 160, 170, 180, 190 or 200 or more wells or well pairs or any value or range of values therebetween in 1 increment that do or do not meet the aforementioned features.

An exemplary embodiment includes some methods, such as, for example, method 4700, which includes method action 4710, which includes obtaining access to a cochlea. Method 4700 further includes method action 4720, which includes delivering a therapeutic substance to a cochlea of a recipient by elution from a cochlear implant electrode array carrier, wherein an elution rate by weight over a period of time is variable owing to a geometry of the carrier containing the therapeutic substance. In an exemplary embodiment, the geometry can be the geometry as detailed herein with respect to the width and/or the depth of the cavities being different. In this regard, the elution rate of X milligrams per hour is the case for a first subsection of the period of time (first 5 days, for example), and the rate varies to a rate of Y milligrams per hour for a second subsection of the period of time (10 days, for example). In an exemplary embodiment, the rate can be a volume per time instead of a mass per time. In an exemplary embodiment, the rate can be both.

In embodiments, as will be understood from the teachings above, the variation in the rate is achieved without any active interaction during the method by a healthcare professional or by programming or by a controller, etc. In this regard, the variation is entirely due to the geometry. In an exemplary embodiment the geometries at issue are constant during the period that the method is executed. This is not to say that the physical arrangement does not change. Indeed, the therapeutic substance elutes from the cavity of the void, as detailed above. This is to say that the cavity or void or well geometry does not change. That said, in an exemplary embodiment, any change in the geometry is only a result of the fact that the therapeutic substances leaving the void. In an exemplary embodiment, the overall volume of the cavity or void or well does not change any more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 11.0, 12.0, 13.0, 140, 15.0, 16.0, 17.0, 18.0, 19.0, 20.0, 21.0, 22.0, 23.0, 24.0, 25.0, 26.0, 27.0, 28.0, 29.0, 30.0, 31, 32, 33, 34, 35, 36, 37, 38, 39, or 40% or any value or range of values therebetween in 1% increments relative to that which is the case at the beginning of the method. The method can begin at the time that the implant is made, inserted into the cochlea, any of the beginnings detailed above (e.g., after wound closure, a period of time after such, etc.), and can last any of the temporal periods detailed above (and can extend beyond such—method action 4720 can be executed for a first period of time, and it can continue after such, in some embodiments).

In an exemplary embodiment, the action of delivering the therapeutic substance is executed without a pump and without active control of therapeutic substance delivery mechanisms. In an exemplary embodiment, the action of delivering the therapeutic substance is executed solely by passive activities.

In an exemplary embodiment the geometry is a static geometry with time during the time that the rate varies. The times can be any of the times herein.

In an exemplary embodiment of the method 4700, the elution rate by weight is variable because, as the substance elutes from locations further away from a surface of the carrier member, an amount of substance exposed due to prior elution at given location is different than at other location(s) previously eluted therefrom. In an exemplary embodiment, the elution rate by weight is variable because a surface area of the substance exposed as elution takes place is different at different temporal periods. The surface area can be the areas detailed above/can change according to the teachings detailed above. In an exemplary embodiment, the surface area is the area that is established by the well with respect to a plane that is normal to the longitudinal axis of the well. In view of the teachings herein, it can be seen that the elution rate of method 4700 is variable owing to a changing total surface area of therapeutic substance exposed to fluid in the cochlea with time.

In an exemplary embodiment, the carrier used in method 4700 includes a plurality of wells, the wells having at least one of different respective depths relative to other wells or different respective widths relative to other wells at different respective depths of the respective wells. This can be a feature that can enable the elution rate to be variable over the period of times owing to the geometry of the carrier.

Figure 48:
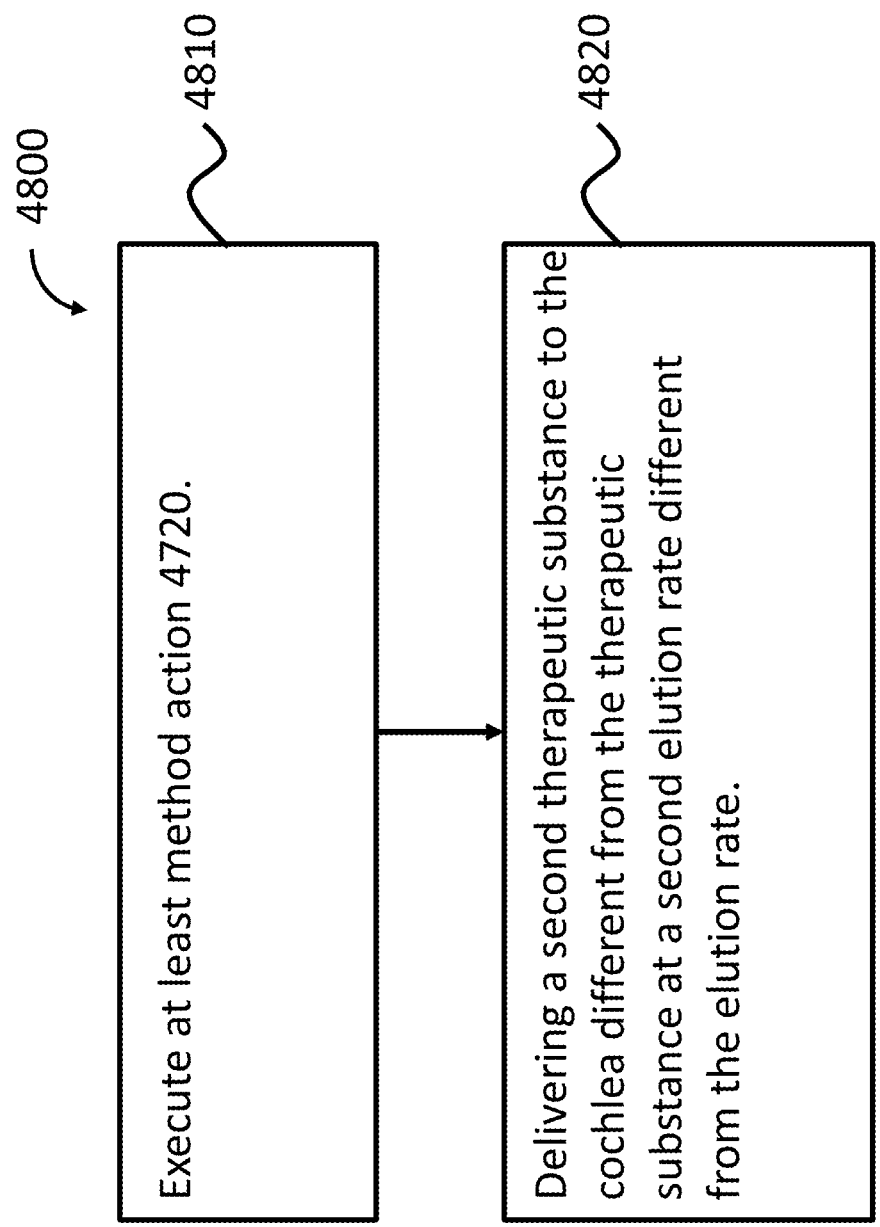

FIG. 48 presents another exemplary flowchart for an exemplary method, method 4800, which includes method action 4810, which includes executing at least method action 4720 of method 4700. Method 4800 further includes method action 4820, which includes delivering a second therapeutic substance to the cochlea different from the therapeutic substance at a second elution rate different from the elution rate. This can be done at a temporally overlapping. With respect to the therapeutic substance of method action 4720 or could be completely separate therefrom. This could occur during the temporal period where one completely overlaps the other, where one only partially overlaps the other, etc. In an exemplary embodiment, the time period associated with the first rate overlaps with the time period associated with the second rate by, with respect to the length of time of the period associated with the first rate, less than greater than or equal to 0, 5, 10, 15, 20, 25, 30, 35, 40, 45, 50, 55, 60, 65, 70, 75, 80, 85, 90, 95 or 100% or any value or range of values therebetween in 1% increments and/or vice versa (e.g., 25 percent of the first time period). That said, in an exemplary embodiment, the temporal period between the two where such do not overlap can be, with respect to the length of time of the period associated with the first rate, less than greater than or equal to 0, 5, 10, 15, 20, 25, 30, 35, 40, 45, 50, 55, 60, 65, 70, 75, 80, 85, 90, 95, or 100%.

Figure 49:
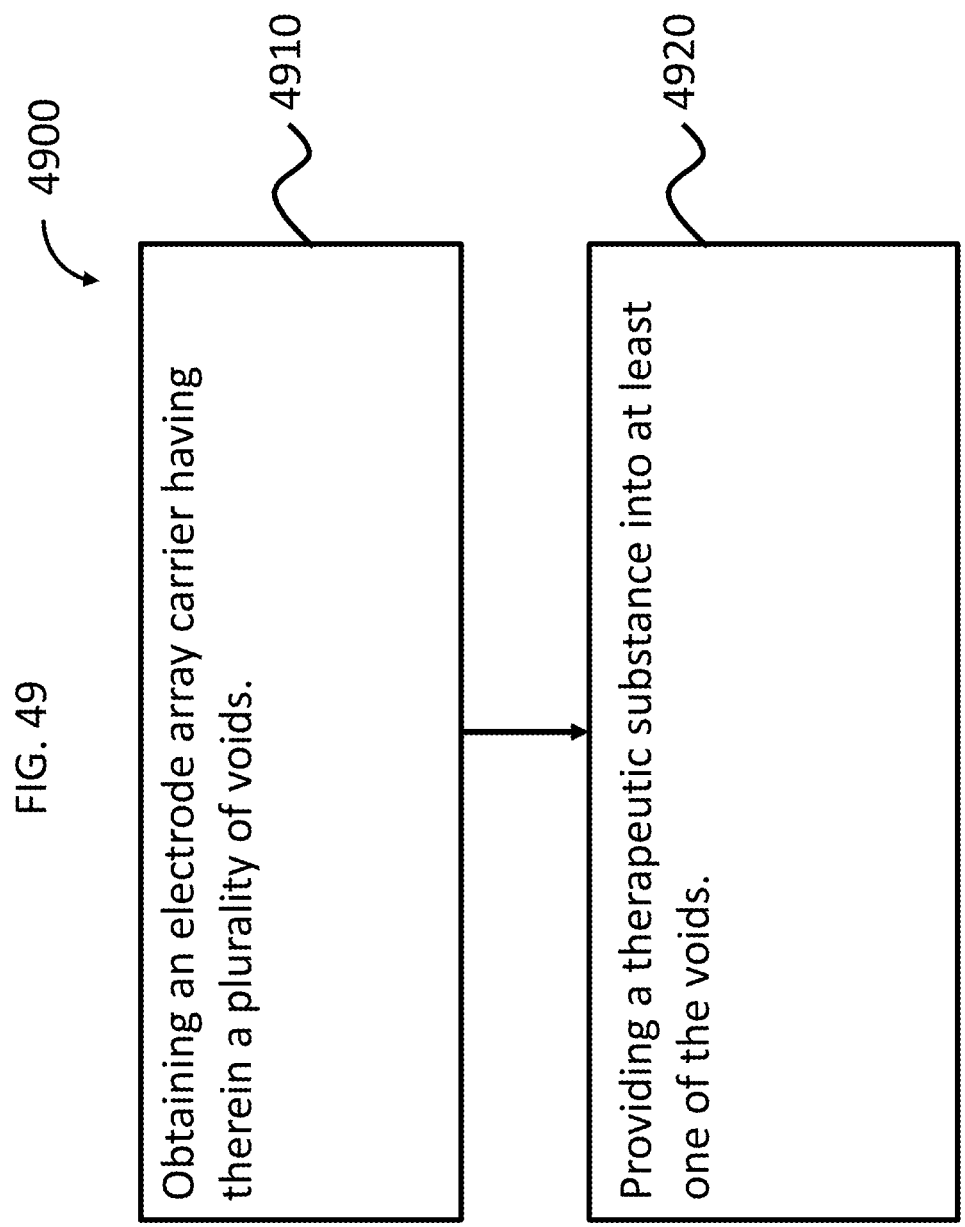

FIG. 49 presents another exemplary flowchart for an exemplary method, method 4900, which includes method action 4910, which includes the action of obtaining an electrode array carrier having therein a plurality of voids. In an exemplary embodiment, the electrode array carrier is a stock electrode carrier and the voids are common to other electrode array carriers of the stock. In an exemplary embodiment, the electrode array carrier is design identical (i.e., tolerancing differences may exist) to at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130 or 140 or more or any value or range of values therebetween in 1 increment carriers in existence at the time of obtaining (note that this refers to the carrier and voids—the fact that there is or is not something in the voids is irrelevant to this issue, even if such expands or contracts the voids—this a design identical feature). In an exemplary embodiment, the action of obtaining corresponds to the action of making.

Method 4900 also includes method action 4920, which includes providing a therapeutic substance into at least one of the voids. In an exemplary embodiment, the action of providing the therapeutic substance into the at least one of the voids results in a specific therapeutic substance delivery profile when the electrode array carrier is implanted in a human, all other things being equal. Conversely, in other embodiments, the action of providing the therapeutic substance into the at least one of the voids results in a general therapeutic substance delivery profile when the electrode array carrier is implanted in a human. In an exemplary embodiment, the action of providing the therapeutic substance into the at least one of the voids results in a therapeutic substance delivery profile that is different from at least 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130 or 140 or more, or any value or range of values therebetween in 1 increment from a previous profile and/or from a subsequent profile that resulted from or results from the execution of the method by an entity performing the method with a different array carrier (this difference can be based on a statistically constant person—a hypothetical person having certain characteristics, thus delinking differences in physiology from the resulting product—for example, a model cochlea can be used, such, as for example, a beaker with a known solution therein that represents perilymph at a pressure and temperature, etc.). In an exemplary embodiment, this comparison is within 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130 or 140 days or weeks or months from when method 4920 is executed. In an exemplary embodiment, the comparison carriers are made from the same manufacturer and/or are made at the same location or otherwise originated from the same manufacturing location.

In an exemplary embodiment of method 4900, the mechanical properties of the electrode array carrier are compatible for implantation into a cochlea of the human before and after method action 4920 and comparable to other electrode array carriers where different therapeutic substance arrangements were provided to the carrier, such as any of the other comparison carriers noted above. In an exemplary embodiment, the action of providing the therapeutic substance is executed while the electrode array carrier is curled. In an exemplary embodiment, the carrier is for a curled electrode array and method action 4920 is executed without providing any substantial stress on the carrier and/or with the carrier in its relaxed state. That said, in an alternate embodiment, method action 4920 is executed with a curly electrode array that is stressed or otherwise held in a straightened state.

In an exemplary embodiment, method action 4920 includes executing such that therapeutic substance delivery is precisely tailored for specific cochlea locations once inserted into the cochlea of the human relative to other cochlea locations if the action of providing the therapeutic substance was executed differently and the electrode array carrier was located in the same location within the cochlea.

In an exemplary embodiment, this can be achieved by, for example, loading or otherwise providing therapeutic substance in some of the voids but not others. In an exemplary embodiment, this can be achieved by any of the actions detailed herein that would enable such unless otherwise indicated.

In an exemplary embodiment, method action 4920 includes providing at least 2, 3, 4, 5, 6, 7, 8, 9, or 10 different therapeutic substances instead of providing less or more substances, such as, only one therapeutic substance, and the actor(s) executing method action 4920 have at least one of previously provided or later provided less or more substances, such as only one therapeutic substance on another carrier, such as of the stock and/or of the other comparison carriers detailed above such that the carrier of the stock/comparison was implanted in a human with the less or more, such as only one therapeutic substance.

Consistent with some of the teachings above, an exemplary embodiment of method 4900 includes applying a silicone over one or more of the voids after the action of providing the therapeutic substance to obtain a slower release of the substance relative to that which would otherwise be the case.

In an exemplary embodiment of method 4900, the voids are wells have a varying diameter normal to a longitudinal axis thereof with respect to location along the longitudinal axis and/or the action of providing the therapeutic substance into the well includes placing such into the well to a height that the varying diameter in combination with the height provides a specific desired release regime from that well. In some embodiments, the action of providing the therapeutic substance is executed at a facility were the carrier is implanted in a human. In some embodiments, the methods detailed herein are executed 1, 2, 3, 4, 5, 6, 7, 8, 9, 10, 11, 12, 13, 14, 15, 16, 17, 18, 19, 20, 25, 30, 35, 40, 45, or 50 times, or any value or range of values therebetween in one increment, and such can be executed at the same facility and/or at different facilities. In an exemplary embodiment, the method actions detailed herein further include implanting the cochlear implant electrode array that includes the carrier after executing one or more or all of the method actions detailed herein. In an exemplary embodiment, the entity that implants electrode array into the recipient is the same as the entity that executed at least one other method action detailed herein.

In view of the above teachings, there is an exemplary method, wherein there are a plurality of voids spaced apart from one another, a first group of voids numbering between 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 or more or any value or range of values therebetween in 1 increment (e.g., between 2 and 10, between 5 and 44, etc.) have a first general depth and width profile (wherein the between includes the bounding numbers and/or a second group of voids numbering between 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 or more or any value or range of values therebetween in 1 increment (e.g., between 2 and 10, between 5 and 44, etc.) have a second general depth and width profile different from the first general depth and width profile and/or a third group of wells numbering between 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 or more or any value or range of values therebetween in 1 increment (e.g., between 2 and 10, between 5 and 44, etc.) have a third general depth and width profile different from the second general depth and width profile, and/or a fourth group of voids numbering between 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 or more or any value or range of values therebetween in 1 increment (e.g., between 2 and 10, between 5 and 44, etc.) have a fourth general depth and width profile different from the third general depth and width profile and/or a fifth group of voids numbering between 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 or more or any value or range of values therebetween in 1 increment (e.g., between 2 and 10, between 5 and 44, etc.) have a fifth general depth and width profile different from the fourth general depth and width profile and so on for, for example, a $6^{th}$, $7^{th}$, $8^{th}$, and $9^{th}$ such group, and the action of providing the therapeutic substance includes choosing voids in one or more of the groups into which therapeutic substance is provided relative to others so that the specific therapeutic substance delivery profile is achieved when the electrode array carrier is implanted in a human that would be different if other voids are chosen for an overall same amount by weight of therapeutic substance.

Figure 39:
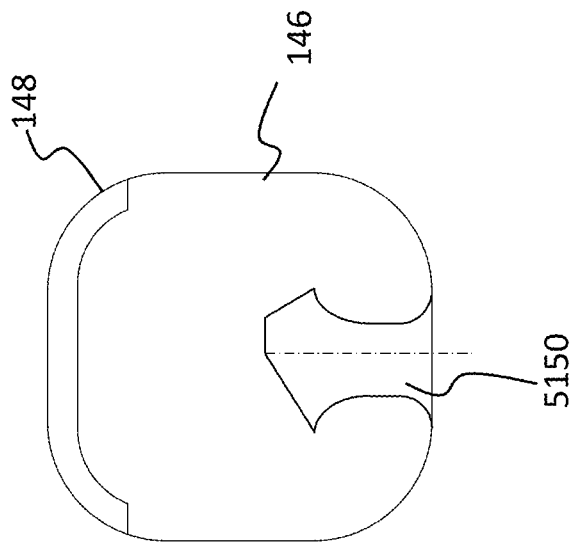
Figure 41:
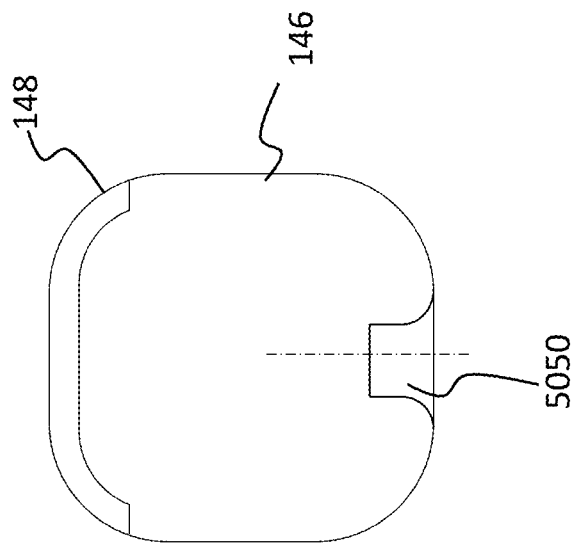

FIGS. 41 and 39 present some alternate exemplary wells, 5050 and 5150, according to an exemplary embodiment. It can be seen that these wells can utilize a curved arrangement as opposed to a straight arrangement, at least in some instances.

At least some exemplary embodiments can be configured with voids according to at least some of the teachings detailed herein which provide an initial spike or an initial aggressive delivery regime of a therapeutic substance, followed by a less aggressive or a more moderate delivery a regime thereafter. This can be achieved by, for example, the embodiment of FIG. 41, where the parabolic sidewalls relatively quickly reduce the amount of therapeutic substance that is exposed to body fluids, at least in a rate that is faster than if the overall change in area to the constant area was achieved via flat walls.

It is also noted that at least some exemplary embodiments can be arranged so that the delivery rates are rates that are within a safe delivery regime. In this regard, it can be seen that in at least some exemplary embodiments, the shapes of the voids can be arranged so that the amount of therapeutic substance that is delivered always falls at and/or below a given rate, which rate can be a rate that is safe, at least statistically. Conversely, there is also utilitarian value with respect to providing therapeutic substance at a rate that is effective. Accordingly, at least some exemplary embodiments utilize voids having configurations that balance the safety and the efficacy according to a desired regime.

It is also noted that in at least some exemplary embodiments, the fact that the therapeutic substance may have to elute through more amounts of material within the voids as time goes on, owing to the location of the therapeutic substance, can also be taken into account with respect to achieving the delivery rates detailed herein.

In an exemplary embodiment, can be seen that some embodiments result in the avoidance of linear scaling of delivery of therapeutic substance with respect to different stages. Accordingly, some exemplary embodiments avoid linearly scaling of delivery rates with respect to staging of therapeutic substance delivery.

It is briefly noted that in an exemplary embodiment, the overall volume of a given well can be the same as that of another given well, and the same exact therapeutic substance dose can be located in both of the wells, but different elution characteristics will be present. In view of the above, it is to be understood that cumulative release rates of therapeutic substance can be controlled or otherwise varied by exposed therapeutic substance loaded silicone surface area and/or thickness thereof. Also, by altering the shapes of the well walls, it can be seen that the ability to control the therapeutic substance release profile can be achieved. Moreover, precise drug release profiles can be achieved at separate locations in the cochlea.

Embodiments can enable the tuning, and thus include the action of tuning, the amount and/or location of drug loaded silicone on electrode arrays without impacting the mechanical properties thereof. By tailoring the well geometries and/or the void geometries, such as by making them fatter or deeper and variations there between, a change in the elution profile over long and/or short times can be achieved. In an exemplary embodiment, burst release profiles can be achieved and/or relatively no including no release profiles can also be achieved.

In at least some exemplary embodiments, the therapeutic substances located in the voids are not so-called drug pieces. In this regard, in some instances, no pellets or blocks of a drug or otherwise therapeutic substance can be placed into voids in an electrode array. Here, in an exemplary embodiment, the voids are loaded with silicone and the therapeutic substance, nothing else. This is different from the utilization of drug pieces. In an exemplary embodiment, the voids are filled or otherwise loaded via movement of a fluid and/or a semi fluid material, such as a gel. In an exemplary embodiment, the voids are filled via movement that excludes the movement of a solid material (other than the machine to move the material, of course). While some teachings detailed above have been directed towards the application of teachings herein to a curly electrode array, it is also noted that the teachings detailed herein can be applied with respect to a straight electrode array.

In an exemplary embodiment, the action of providing the therapeutic substance is executed by flowing at least a semi-liquid substance (which includes a liquid substance) containing the therapeutic substance into the voids.

In an exemplary embodiment, the material is manually deposited/flowed into each well, then manipulate it to the edges of the well with a tool or pair of tweezers using the meniscus or surface tension to manipulate it accurately within the geometry of the well, this is done on one side of the electrode whilst it is held securely, then we cure and repeat for the other side, see image below, this could be likened to painting tin soldiers/toys if you are looking to be creative, we also have designed the well features with automation in mind and would envisage that this could be automated not much differently from how state of the art automated liquid handling robotics currently work today with the correct viscosity, there are a number of ways to control viscosity or make silicone/therapeutic substances less viscous if required, but will not detail here.

In an exemplary embodiment, the action of providing the therapeutic substance can be executed by manually depositing and/or flowing an amount of the semi-liquid material into a given void, and then manipulating the material to edges of the well with a tool or pair of tweezers, such as by using the meniscus or surface tension to manipulate the material accurately or otherwise utilitarianly within the geometry of the well or void. This can be done on one side of the electrode array carrier (such as for embodiments where there are voids on multiple sides of the array, while it is held securely, and subsequently cured and then repeated for the other side, repeat for the other side.

In some embodiments, automation is used to charge/provide the material into the voids. By way of example, an automated liquid handling robotic could be utilized in some methods, if the correct and/or utilitarian viscosity is used/controlled and/or the silicone/therapeutic substances are made more or less viscous as needed for automation. In this regard, in at least some exemplary embodiments, the methods include adjusting the viscosity of the therapeutic substance containing material so as to provide the material and the voids.

Figure 50:
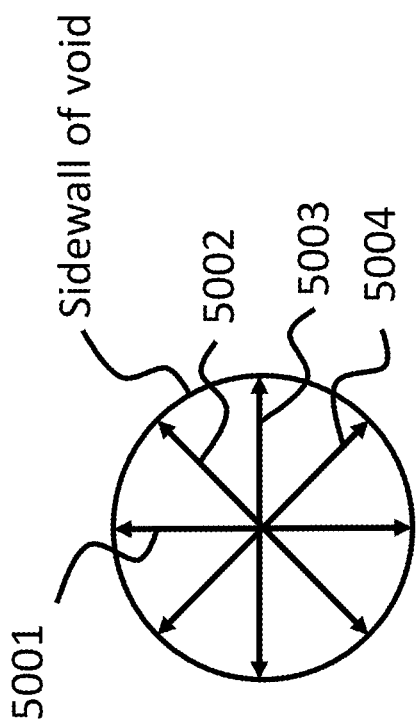

In an exemplary embodiment, when measured on a plane that is normal to a longitudinal axis 999 of the well, a given cross-section of a void can have an interior wall geometry according to the model of FIG. 50, where distances represented by arrows 5001, 5002, 5003, and 5004, which arrows are 45 degrees from each other, and extend from side of the wall to the other, can be variously greater than, less than or equal to 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950, 1000 or more, or any value or range of values in 1 increment, $\times 10^{-1}$ mm (i.e., take the recited number and multiply it by 0.1, the listed number of 1, for example, is 0.1 mm). In some embodiments, 5001, 5002, 5003, and 5004 and distances reflective of arrows between them at 1, 2, 3, 4, 5, 6, 7, 8, 9, 10, 11, 12, 13, 14, 15, 16, 17, 18, 19, or 20 degrees (e.g., 180 arrows 1 degree offset from each other) can variously have those values and/or are within 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950, 1000 or more, or any value or range of values therebetween in 1 increments based on the smallest dimension of an arrow. In an exemplary embodiment of a well having a perfectly circular cross-section (potentially hypothetical, in view of tolerancing), all would be within 1%. Conversely, a strap might be such that all are within 950%, for example. This can be applicable to any of the voids herein in some embodiments.

Figure 51:
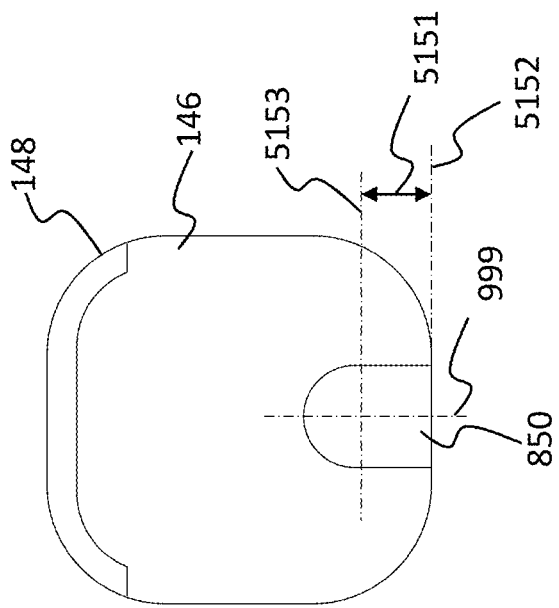
FIGS. 50 and 51 provide some exemplary dimensional references for voids.

The above values can be measured on various planes that are normal to axis 999. FIG. 51 represents an exemplary dimensional arrangement where distance 5151 is measured from the extrapolated tangential surface of the top of the well (if one extrapolates the surface of the carrier to the axis 999, the tangent plane to that extrapolated surface is the bottom dimension 5152), and the plane is on 5153. In an exemplary embodiment, 5151 is 0, 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 650, 700, 750, 800, 850, 900, 950, 1000 or more or any value or range of values in 1 increment$\times 10^{-2}$ mm (e.g., 0.01 mm, 7.51 mm). There can be 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 or more or any value or range of values therebetween in 1 increments planes in some embodiments.

Figure 52:
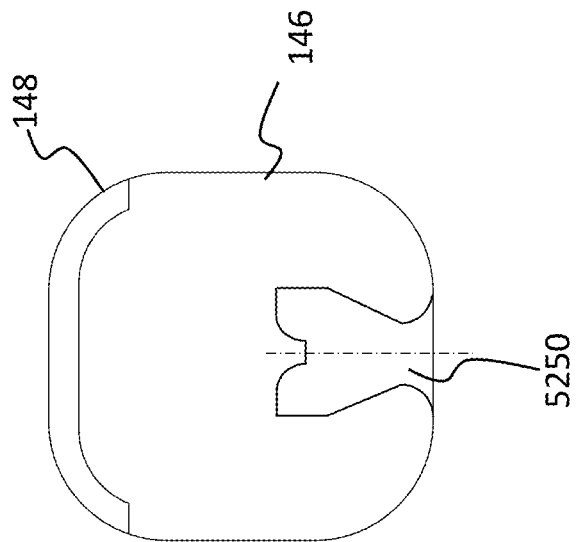

In an exemplary embodiment, the wells or the voids can have a compound bottom surface, such as a wine bottle, or the like, as seen, for example, in FIG. 52, with respect to void 5250.

By way of example only and not by way of limitation, the wells can be filled (fully or partially—more on this below) with a composition that includes a therapeutic substance mixed with, by way of example only and not by way of limitation, DDU-4320 excipients grade silicone and/or D125 grade, etc. By way of example only and not by way of limitation, there can be a mixture of 40% Dexamethasone, with the remainder, silicone or some other inert or non-active ingredient.

In an exemplary embodiment, the electrode array is a curved electrode array.

It is noted that in at least some exemplary embodiments, the therapeutic substance is a liquid-based therapeutic substance. In an exemplary embodiment, the therapeutic substance is devoid of any solid substances, including powdered substances. In an exemplary embodiment, the therapeutic substance is liquid and not solid/not a powder and/or not a salt-based substance or the like. Further, the teachings detailed herein are directed towards, in at least some in exemplary embodiments, non-capsule based therapeutic substance delivery. In an exemplary embodiment, at least 30, 35, 40, 45, 50, 55, 60, 65, 70, 75, 80, 85, 86, 87, 88, 89, 90, 91, 92, 93, 94, 95, 96, 97, 98, 99 or 100% or any value or range of values therebetween in 1% increments of the therapeutic substance that is delivered from one or more of the voids disclosed herein and/or from the overall electrode array while located in the cochlea occurs as a result of elution and/or does not occur as a result of flow of the therapeutic substance as a result of pressure differences, etc. In an exemplary embodiment, it is impossible to control the rate of elution and/or drug delivery after the electrode array is implanted in the cochlea beyond removing the electrode array from the cochlea.

There is also an exemplary embodiment where the voids (wells or otherwise) have different opening areas and/or volumes and/or different eluting properties (e.g., rate of elution, etc.) along the length of the electrode array that vary according to a regime, and, in some embodiments, the variation is spatial correlation with the tapered anatomy of the scala tympani. In an exemplary embodiment, the differences enable the delivery of varied doses and/or control the drug concentration in the scala tympani, such as in a uniform manner, to take into account that the local volume of the scala tympani varies with distance (decreases from the basal to apical). In one such embodiment, the well surface area and/or well volume of a given well decreases from basal to apical such that the drug concentration will be uniform in the scala tympani. By way of example only and not by way of limitation, in embodiments where the area of the opening of the voids and/or cavities and/or wells controls the release rate, and thus the mass and/or volume of the therapeutic substance that is delivered over a given period of time from a given location along the electrode array, by reducing the area of the opening at locations that are more apical along the array, all other things being equal, the less or otherwise the lower the release rate will be, and thus the lower the amount of therapeutic substance that will be delivered at that location the cochlea, all other things being equal, relative to other locations.

In an exemplary embodiment, there are 1, 2, 3, 4, 5, 6, 7, 8, 9, 10, 11, 12, 13, 14, 15, 16, 17, 18, 19 or 20 or more arbitrary regions of the electrode array that encompass the entire array at that region (e.g., all the way around) that are part of the intra-cochlear portion, spaced along the longitudinal axis, that respectively include any of 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 or more voids, respectively having singularly or collectively any of the volumes and/or opening areas and/or opening geometries or volume geometries or otherwise any of the geometries, disclosed herein. These regions can be contiguous and/or spaced apparat from one another and can have, at least depending on the number, a length in the longitudinal axis of 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200 or more, or any value or range of values in 1 increment, $\times 10^{-1}$ mm (i.e., take the recited number and multiply it by 0.1, the listed number of 1, for example, is 0.1 mm) or any value or range of values in 1 increment, $\times 10^{-1}$ mm (i.e., take the recited number and multiply it by 0.1, the listed number of 1, for example, is 0.1 mm). The spacing between one or more of these regions can also be any of the just detailed numbers.

The idea here is that in a first region, the volumes and/or areas and/or number of voids are larger than in a second region in the distal direction, and the second region has volumes and/or areas and/or a number of voids that are larger than in the third region in a distal direction, and so on. By varying the volumes and/or areas and/or number of voids in this manner, the amount of therapeutic substance that is delivered at the local locations adjacent the regions will be different with respect to mass and/or volume and/or rate of delivery, but because the cochlea tapers and thus has a smaller local volume with location in the cochlea, the amount of therapeutic substance per unit volume of the cochlea is normalized or otherwise constant relative to that which would have otherwise been the case if the volumes and/or surface areas were constant over the regions.

In an exemplary embodiment, any one or more of the regions has a volume in total of the voids and/or a total surface area opening and/or a total number of voids that is no more than 1, 2, 3, 4, 5, 6, 7, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of the total in the region more basil thereto.

In an exemplary embodiment, the variations in the area and/or volume and/or release rate is correlated to the cross-sectional area of the scala tympani normal to a longitudinal axis thereof corresponds to a one to one relationship (e.g., if the cross-sectional area is reduced by half, the opening area for a given section and/or the volume and/or release rate for a given section is also reduced by half). In an exemplary embodiment, the variations occur in something different than a one-to-one relationship, such as about a 0.1, 0.2, 0.3, 0.4, 0.5, 0.6. 0.7, 0.8. 0.9, 1.0, 1.1, 1.2, 1.3, 1.4, 1.5, 1.6. 1.7, 1.8, 1.9 or 2.0 or any value or range of values therebetween in 0.01 increments to 1 relationship. Note also that the variation need not necessarily be linear and/or be constant or otherwise follow a given pattern (exponential or geometric, for example—any correlation that can enable the teachings detailed herein can be utilized at least some exemplary embodiments).

It is noted that any method of transport of the therapeutic substance out of the wells/voids can be utilized, where such is passive, such as, for example, elution, diffusion, dissolution, etc. (where some may not be mutually exclusive). It is further noted that some embodiments include voids having a volume established by the extrapolated surface from the side of the voids that equals any of the depths multiplied by cross-sectional area that is circular having a diameter according to any of the widths herein.

With respect to the embodiments disclosed herein that utilize a silicone in the voids, in at least some exemplary embodiments, the silicone is established and otherwise differentiated from other components of the electrode array assembly by the type of polymer, the molecular weight, the size, such as the cross-section of the eluting material, the silica filler density, a prosody of the elutor, such as a micro/nano porosity, and/or a layered polymer structure. In this regard, the eluting material can be a component that has any one or more of the properties just detailed that results in the component being an elutor and one or more the other components of the electrode array assembly can have one or more of the properties just detailed that results in that component not being an elutor. In view of the above, it can be understood that in at least some exemplary embodiments, there is a passive non-pressurized delivery system configured to deliver the therapeutic substance directly into the cochlea.

It is noted that any disclosure with respect to one or more embodiments detailed herein can be practiced in combination with any other disclosure with respect to one or more other embodiments detailed herein. That is, some exemplary embodiments include any one or more of the teachings detailed herein combined with any one or more the other teachings detailed herein, unless otherwise stated such, providing that the art enables such. It is also noted that any disclosure herein of any feature corresponds to a disclosure of an exemplary embodiment that explicitly excludes that given feature from utilization with any one or more other features detailed herein unless otherwise specified providing that the art enables such.

It is noted that any disclosure herein of any method action corresponds to a disclosure of a device and/or system that enables that method action. It is noted that any disclosure herein of any method of manufacturing or otherwise developing or making a device disclosed herein corresponds to a disclosure of the resulting device that results from that method. It is noted that any disclosure herein of any apparatus and/or system corresponds to a disclosure of providing and/or making that apparatus and/or system. It is noted that any disclosure herein of any functionality corresponds to a device and/or system is configured to provide that functionality. It is noted that any disclosure of any device and/or system herein corresponds to a disclosure of a method of utilizing that device and/or system.

In this regard, it is noted that any disclosure of a device and/or system herein also corresponds to a disclosure of utilizing the device and/or system detailed herein, at least in a manner to exploit the functionality thereof. Further, it is noted that any disclosure of a method of manufacturing corresponds to a disclosure of a device and/or system resulting from that method of manufacturing. It is also noted that any disclosure of a device and/or system herein corresponds to a disclosure of manufacturing that device and/or system.

Any method action disclosed herein can be executed in any order relative to another method action disclosed herein unless otherwise noted and/or unless the art does not enable such. Any disclosure herein of a method that includes a method action also in includes a disclosure of a method that excludes that method action in at least some exemplary embodiments.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A device, comprising:
an electrode array carrier; and
therapeutic substance, wherein
the therapeutic substance is located in a well of the electrode array carrier.

2. The device of claim 1, wherein:
the well is deeper than a maximum width.

3. The device of claim 1, wherein:
the carrier is made of silicone; and
the well is at least partially filled with a silicone-medicament mixture distinct from the silicone of the carrier, the medicament of the medicament mixture being the therapeutic substance.

4. The device of claim 1, wherein:
there are a plurality of wells spaced apart from one another; and
at least most of the wells of the device are located away from a plane extending through a longitudinal axis of the carrier and electrodes of the carrier.

5. The device of claim 1, wherein:
there are a plurality of wells spaced apart from one another;
a first group of wells numbering between 2 and 10 have a first general depth and width profile;
a second group of wells numbering between 2 and 10 have a second general depth and width profile different from the first general depth and width profile;
a third group of wells numbering between 2 and 10 have a third general depth and width profile different from the second general depth and width profile; and
at least one of:
one or two of the first, second and third group is at least mostly devoid of therapeutic substance;
one or two of the first, second and third group is at least mostly full of therapeutic substance;
one or two of the first, second and third group contains a different therapeutic substance than that contained in one or two of the first, second or third group.

6. The device of claim 1, wherein:
the well is located such that any stress that exists in the array as a result of implantation of the array into a cochlea has no effective impact on the well, all other things being equal.

7. The device of claim 1, wherein:
the well is located such that any stress that exists in the array as a result of implantation of the array into a cochlea has an effective impact on the well, all other things being equal.

8. The device of claim 2, wherein:
the well has a diameter at an outlet of the well of greater than 0.1 mm.

9. The device of claim 1, wherein:
a width of the well is constant with depth of the well over all of the depth.

10. The device of claim 1, wherein:
the device is a membraneless therapeutic substance delivery device.

11. The device of claim 1, wherein:
the well has a uniform depth with respect to location in the direction of the depth at all locations of the well along a longitudinal axis of the array carrier.

12. The device of claim 1, wherein:
a length of the well is constant with depth of the well over all of the depth.

13. The device of claim 1, wherein:
only the therapeutic substance or a mixture containing the therapeutic substance is located in the well.

14. The device of claim 13, wherein:
the electrode array carrier is arranged so that the therapeutic substance is delivered by dissolution, and wherein the device is cochlear implant electrode array.

15. The device of claim 1, wherein:
the device includes a plurality of wells that are spaced apart from one another, at least some of the wells of the plurality of wells being located singularly relative to other wells of the plurality of wells at a same distance along a longitudinal axis of the carrier.

16. The device of 1, wherein:
there are at least four wells that are spaced apart from one another.

17. The device of claim 1, wherein:
the device is devoid of a backstrap and tip containing a therapeutic substance.

18. A device, comprising:
an electrode array carrier; and
a therapeutic substance, wherein
the therapeutic substance is located in at least one cavity of the carrier, the cavity having at least one of a non-uniform depth or a non-uniform width with respect to location in a direction of the depth.

19. The device of claim 18, wherein:
the cavity has the non-uniform width with respect to the location in the direction of the depth; and
the at least one of the non-uniform depth or the non-uniform width with respect to location in the direction of the depth has an effective impact on a delivery of the therapeutic substance to a human.

20. The device of claim 18, wherein:
the cavity is a well extending from the outer surface of the carrier; and
the at least one of the non-uniform depth or the non-uniform width with respect to location in the direction of the depth has an effective impact on a delivery of the therapeutic substance to a human.

21. The device of claim 18, wherein:
the cavity has an elongate portion that extends in a longitudinal direction of the carrier; and
the at least one of the non-uniform depth or the non-uniform width with respect to location in the direction of the depth has an effective impact on a delivery of the therapeutic substance to a human.

22. The device of claim 18, wherein:
there are at least four cavities having the at least one of a non-uniform depth or a non-uniform width with respect to location in a direction of the depth; and
with respect to the respective cavities of the at least four cavities, the respective at least one of the non-uniform depth or the non-uniform width with respect to location in the direction of the depth has an effective impact on a delivery of the therapeutic substance to a human.

23. The device of claim 18, wherein:
the device is devoid of a backstrap and tip containing a therapeutic substance; and
the at least one of the non-uniform depth or the non-uniform width with respect to location in the direction of the depth has an effective impact on a delivery of the therapeutic substance to a human.

24. The device of claim 18, wherein:
the cavity has a uniform depth with respect to location in the direction of the depth at all locations of the cavity along a longitudinal axis of the array carrier; and
the non-uniform width with respect to location in the direction of the depth has an effective impact on a delivery of the therapeutic substance to a human.

25. The device of claim 18, wherein:
the at least one of the non-uniform depth or the non-uniform width with respect to location in the direction of the depth has an effective impact on a delivery of the therapeutic substance to a human.

26. The device of claim 25, wherein:
the cavity of the carrier has a diameter at an opening of the cavity of greater than 2 mm.

27. The device of claim 18, wherein:
the cavity is more shallow than a maximum width and more shallow than a maximum length; and
the at least one of the non-uniform depth or the non-uniform width with respect to location in the direction of the depth has an effective impact on a delivery of the therapeutic substance to a human.

28. The device of claim 18, wherein:
the cavity of the carrier has a minimum diameter at an opening of the cavity of greater than 0.3 mm.

29. The device of claim 28, wherein:
the cavity of the carrier has a diameter at an opening of the cavity of greater than 2 mm.

30. The device of claim 29, wherein:
the diameter at the opening greater than 2 mm is normal to the minimum diameter.

31. The device of claim 29, wherein:
the at least one of the non-uniform depth or the non-uniform width with respect to location in the direction of the depth has an effective impact on a delivery of the therapeutic substance to a human.

32. The device of claim 28, wherein:
the cavity of the carrier has a diameter at an opening of the cavity of greater than 5 mm.

33. The device of claim 18, wherein
the at least one of the non-uniform depth or the non-uniform width with respect to location in the direction of the depth has an effective impact on a delivery of the therapeutic substance to a human and a distal tip of the device is devoid of a cavity configured to receive a therapeutic substance.

34. The device of claim 18, wherein:
there are at least three cavities in the carrier, and respective cavities of the at least three cavities have a minimum diameter at an opening of the respective cavity of greater than 0.2 mm, and respective cavities of the at least three cavities have a diameter at an opening of the respective cavity of greater than 3 mm.

35. The device of claim 34, wherein:
respective cavities of the at least three cavities are located such that any stress that exists in the array carrier as a result of implantation of the array carrier into a cochlea has no effective impact on respective cavities of the at least three cavities all other things being equal.

36. The device of claim 19, wherein:
the cavity also has the non-uniform depth.

37. The device of claim 19, wherein:
the cavity has the non-uniform width with respect to location in a direction of a longitudinal axis of the electrode array carrier.

38. A device, comprising:
an electrode array carrier; and
a therapeutic substance, wherein
at least one of:
the electrode array carrier and the therapeutic substance are collectively arranged to provide for a therapeutic substance release rate that is variable over time; or
the therapeutic substance is located in a plurality of wells that are spaced apart from one another, at least some of the wells being located in pairs at a same distance along a longitudinal axis of the carrier.

39. The device of claim 38, wherein:
a layer of silicone is located over the therapeutic substance at some locations and not at other locations.

40. The device of claim 38, wherein:
the electrode array carrier includes a well in which the therapeutic substance is located; and
the well has a geometry such that the therapeutic substance therein has a two state release profile owing to the geometry.

41. The device of claim 38, wherein:
the electrode array carrier includes a well in which the therapeutic substance is located; and
the well has a cross-section, lying on a plane that is normal to a longitudinal axis of the carrier, such that the well at least one of widens or narrows with location closer to the longitudinal axis.

42. The device of claim 38, wherein:
the device is devoid of glue holding the therapeutic substance; and
the therapeutic substance is a drug that is mixed in a silicone separate from the electrode array carrier.

43. The device of claim 38, wherein:
the therapeutic substance is located in a plurality of wells that are spaced apart from one another, at least some of the wells being located in pairs at a same distance along a longitudinal axis of the carrier.

44. The device of claim 38, wherein:
the therapeutic substance is located in a plurality of wells that are spaced apart from one another, at least some of the wells being located singularly relative to other wells at a same distance along a longitudinal axis of the carrier.

45. The device of claim 38, wherein:
the electrode array carrier and the therapeutic substance are collectively arranged to provide for the therapeutic substance release rate that is variable over time; and
the therapeutic substance is located in a plurality of wells that are spaced apart from one another.

46. The device of claim 38, wherein:
the electrode array carrier is arranged so that the therapeutic substance is delivered by diffusion.

47. The device of claim 38, wherein:
the electrode array carrier is arranged so that the therapeutic substance is delivered by dissolution, and wherein the device is cochlear implant electrode array.

48. The device of claim 38, wherein:
the electrode array includes a cavity having a circular cross-section lying on a plane normal to a longitudinal axis of the electrode array, in which cavity is located the therapeutic substance; and
the electrode array includes a passageway extending from the cavity to an outside of the electrode array through which the therapeutic substance travels from the cavity to the outside of the electrode array.

* * * * *